(12) United States Patent
Kabanov et al.

(10) Patent No.: US 7,056,532 B1
(45) Date of Patent: *Jun. 6, 2006

(54) COMPOSITIONS FOR DELIVERY OF BIOLOGICAL AGENTS AND METHODS FOR THE PREPARATION THEREOF

(75) Inventors: Alexander V. Kabanov, Omaha, NE (US); Adi Eisenberg, Montreal (CA); Victor A. Kabanov, Moscow (RU)

(73) Assignees: Univ. Nebraska Bd. of Regents, Lincoln, NE (US); Moscow State Univ., Moscow (RU); McGill Univ., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/445,656

(22) PCT Filed: Jun. 11, 1998

(86) PCT No.: PCT/US98/12139

§ 371 (c)(1),
(2), (4) Date: Jul. 17, 2000

(87) PCT Pub. No.: WO98/56334

PCT Pub. Date: Dec. 17, 1998

Related U.S. Application Data

(60) Provisional application No. 60/053,000, filed on Jun. 13, 1997.

(51) Int. Cl.
*A61K 9/10* (2006.01)
*A61K 47/30* (2006.01)

(52) U.S. Cl. .................... 424/486; 424/487
(58) Field of Classification Search .......... 424/195.1, 424/78.1–78.16, 486–87; 514/3, 772.3; 528/354; 510/114

See application file for complete search history.

(56) References Cited

U.S. PATENT DOCUMENTS

| | | | | |
|---|---|---|---|---|
| 5,112,611 A | * | 5/1992 | Ahmad et al. | 424/195.1 |
| 5,171,737 A | * | 12/1992 | Weiner et al. | 514/3 |
| 5,209,922 A | * | 5/1993 | Merianos et al. | |
| 5,410,016 A | * | 4/1995 | Hubbell et al. | 528/354 |
| 5,531,917 A | * | 7/1996 | Nakayama et al. | 510/114 |

FOREIGN PATENT DOCUMENTS

JP 08 165491 6/1996
RU 1 172 237 A 5/1995

OTHER PUBLICATIONS

Polymeric Materials Science and Engineering, vol. 76, No. 227, Apr. 13-17, 1997, p. 227.
Journal of Controlled Release, NL, Elsevier, vol. 39, No. 2, May. 1, 1996.

* cited by examiner

*Primary Examiner*—Edward J. Webman
(74) *Attorney, Agent, or Firm*—Dann, Dorfman, Herrell & Skillman, P.C.

(57) ABSTRACT

A composition for facilitating delivery of biological agents, comprising a supramolecular complex including as constituents a block copolymer, having at least one nonionic, water soluble segment and at least one polyionic segment, and at least one charged surfactant having hydrophobic groups, the charge of the surfactant being opposite to that of the polyionic segment of the block copolymer. The constituents of the complex are bound by interaction between the opposite charges thereof and between surfactant hydrophobic groups. The complex may include an anionic surfactant having a biological activity, in which case the net charge of such anionic surfactant is no more than about 10.

24 Claims, 5 Drawing Sheets

COMPOSITIONS FOR DELIVERY OF BIOLOGICAL AGENTS AND METHODS FOR THE PREPARATION THEREOF

This applications claims the benefit of provisional application 60/053,000 filed Aug. 13, 1997.

Pursuant to 35 U.S.C. §202(c), it is hereby acknowledged that the U.S. Government has certain rights in the invention described herein, which was made in part with funds from the National Science Foundation under Grant No. DMR-9502807.

FIELD OF THE INVENTION

The present invention relates to compositions for the delivery of biologically active substances, including, without limitation, therapeutic and diagnostic agents, and in particular to compositions comprising block ionomers and oppositely charge surfactants that exhibit combined properties of amphiphilic block copolymers and polyelectrolyte-surfactant complexes.

DESCRIPTION OF RELATED ART

Polyelectrolyte complexes from DNA and a block ionomer containing a nonionic water soluble segment, e.g., poly(ethylene oxide) (PEO), and a polycation segment have been recently proposed to facilitate delivery of macromolecules, e.g., nucleic acids, into living cells, as a means of implementing gene therapy. In these complexes, the charges of the DNA are neutralized by the polycation segments while the complex remains soluble due to the effect of the PEO segments. Such systems belong to a broader class of polyelectrolyte complexes formed by block ionomers. Published reports on complexes from PEO-b-poly(L-lysine) cation and PEO-b-poly($\alpha$-$\beta$-aspartate) anion, as well as PEO-b-polymethacrylate anion and poly(N-ethyl-4-vinylpyridinium) cation have suggested that they represent a new type of chemical entity, with combined properties of amphiphilic block copolymers and polyelectrolyte complexes. Such systems are reported to be stable and soluble in aqueous solution and can form a microphase from the neutralized polyion segments surrounded by a shell from PEO segments. In addition, these complexes appear to form micelle-like aggregates with a concentration dependence resembling those characterized by a critical micelle concentration (CMC). At the same time, these systems behave like regular polyelectrolyte complexes, in that they are salt-sensitive since they tend to dissociate as the salt concentration increases beyond a critical value. Furthermore, they have been shown to participate in substitution reactions involving neutralized polyion segments. These systems are produced as a result of a polyion coupling reaction after mixing polyelectrolyte components. The stability of such systems critically depends on the number of the salt bonds between interacting polyelectrolytes of opposite charge. It takes at least ten salt bonds to form a cooperative system (Papisov and Litmanovich, *Adv. Polym. Sci.,* 1988, 90: 139). Preferably, the number of salt bonds should be twenty or more. This means that the complexes do not form if the net charge of the molecules is less that the minimal number needed to form the required number of salt bonds, i.e., less than 10 to 20. If it is assumed that a minimal molecular mass of a charged unit in the molecule of a polyelectrolyte is about 70, then the molecular mass of the components in such system should be more than about 700, preferably more than about 1,400. In practice, however, many charged units have molecular masses of about 200 and more. Furthermore, many interacting molecules are weak bases or acids that at physiological pH are charged 20 to 30%. This shall put the minimal molecular mass of polyions in these systems at least 3 to 5 times higher, i.e., at least about 2,000 to 7,000. Normally, the molecular masses of polynucleotides used in such systems are 8,000 to 10,000 and more. These systems, therefore, have a fundamental limitation in that they cannot be formed with substances having less than about 10–20 charges and molecular masses less than about 2,000–7,000.

SUMMARY OF THE INVENTION

In accordance with one aspect of the present invention, there is provided a composition of matter comprising a supramolecular complex comprising as constituents a block copolymer, having at least one nonionic, water soluble segment and at least one polyionic segment, and at least one charged surfactant having hydrophobic groups, with the charge of the surfactant being opposite to the charge of the polyionic segment of the block copolymer. The constituents of the complex are bound by interaction between the opposite charges thereof and between surfactant hydrophobic groups. In compositions of the invention comprising an anionic surfactant having biological activity, however, such anionic surfactant has a net charge of no more than about 10, preferably 5.

The polyionic segment of the block copolymer may be polyanionic, in which case the surfactant is a cationic surfactant, or polycationic, in which case the surfactant is an anionic surfactant.

In accordance with another aspect of the present invention, a method is provided for preparation of the above-described composition in the form of vesicles. In performing the method of the invention a block copolymer, having at least one nonionic, water soluble segment and at least one polyionic segment is mixed with a charged surfactant having hydrophobic groups, with the charge of the surfactant being opposite to the charge of the polyionic segment of the block copolymer. The ratio of the net charge of the surfactant to the net charge of the polyionic segment present in the block copolymer is between about 0.01 and about 100.

The compositions of the present invention afford many advantages over the above-mentioned, previously reported block ionomer-polyelectrolyte complexes. For example, the compositions of this invention can be used to improve the therapeutic index with relatively low-molecular mass biological agents, and biological agents having less than 10 charges. Further, they can facilitate administration of biological agents by increasing their aqueous solubility. They also increase the stability and decrease side effects of the biological agents in the body. They further increase bioavailability of the biological agent incorporated therein, after administration to the body. In addition the compositions of the invention provide for site-specific drug delivery and release in the sites with acidic pH, such as tumors, bacteria, stomach, muscle tissues, or sites with alkali pH such as the gastrointestinal tract. They further provide for compartment-specific delivery of both macromolecule and small molecule biological agents into cells by releasing the biological agent in early endosomes, and enhancing its transport in the cytoplasm and cellular compartments.

BRIEF DESCRIPTION OF THE DRAWINGS

FIG. 1 is a graphical representation of binding isotherms of cetylpyridinium bromide (1) and dodecylpyridinium bromide (2) to polyethylene oxide-block-poly(sodium methacrylate), in which β, a fraction of occupied binding sites, is plotted as a function of surfactant concentration.

Figure 4A:
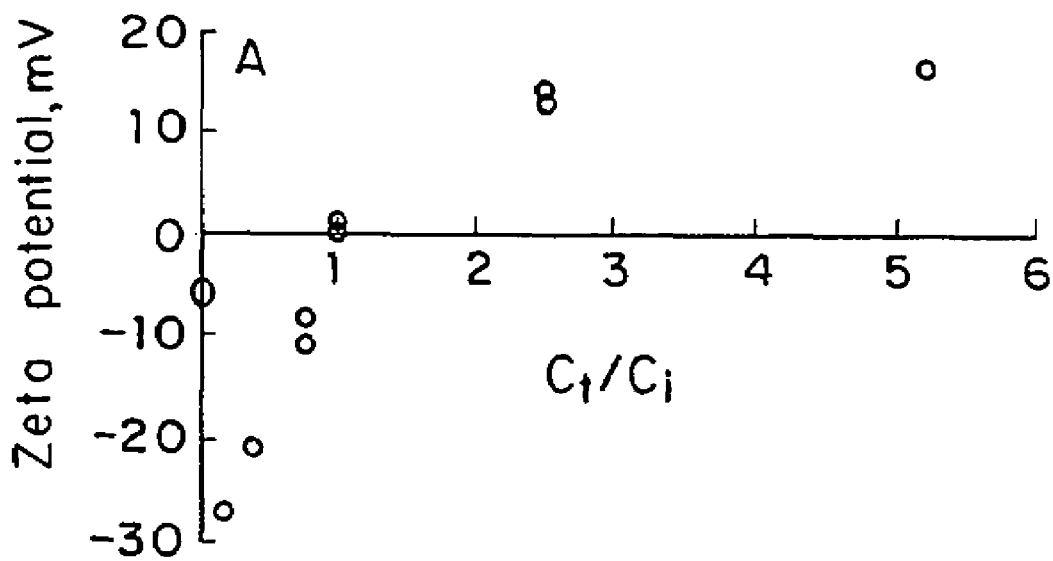
Figure 4B:
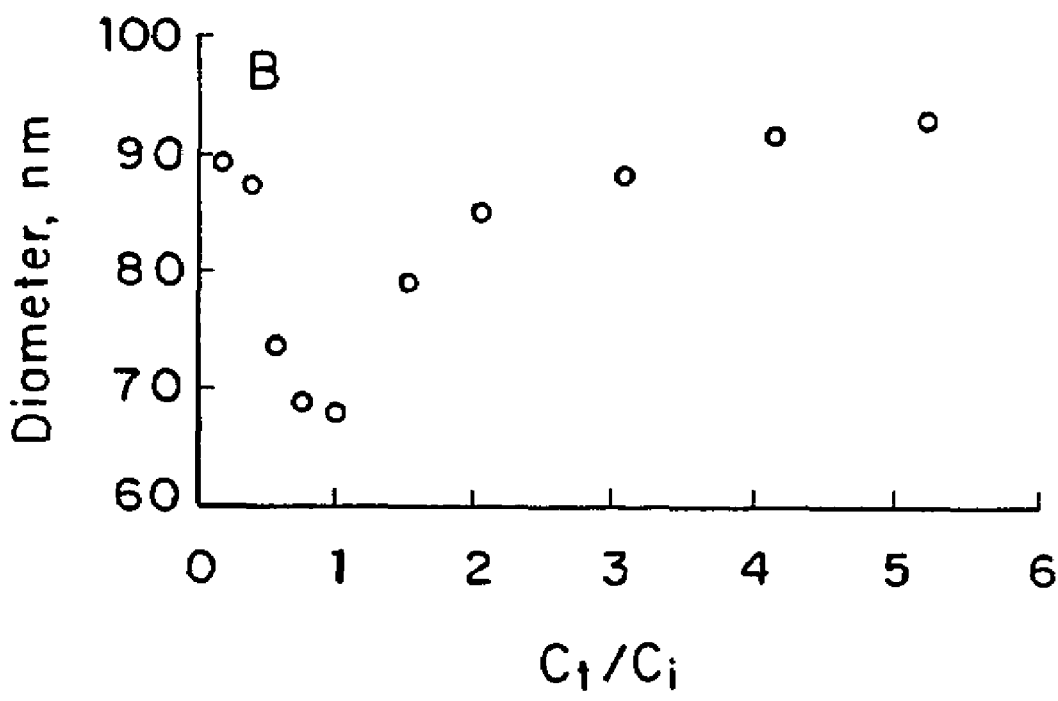

FIG. 4 graphically illustrates the zeta potential (FIG. 4a) and effective diameter (FIG. 4b) of particles formed in the mixture of cetylpyridinium bromide and poly(sodium methacrylate) at various ratios of the surfactant to the ionic units of block copolymer.

Figure 5:
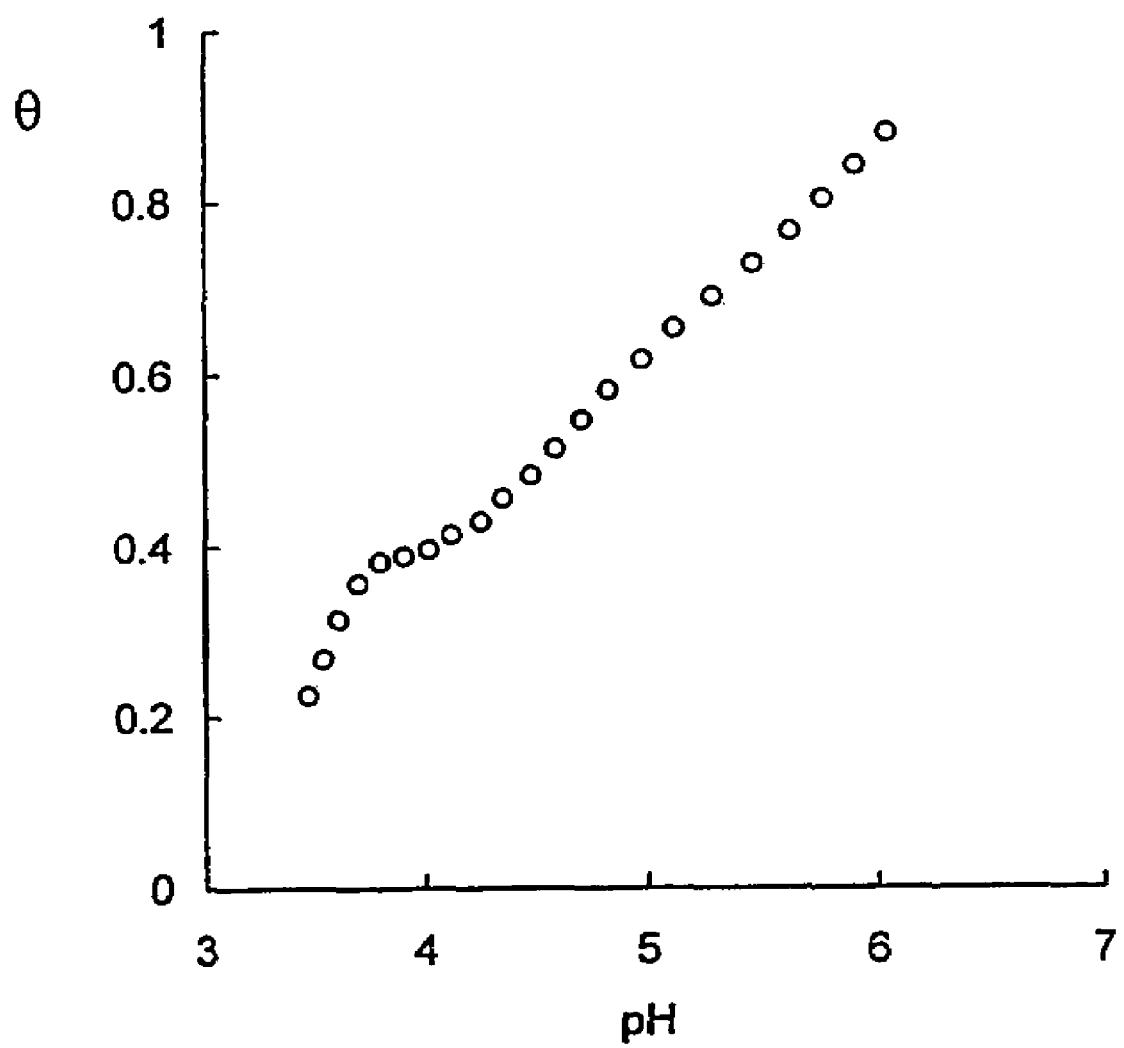

FIG. 5 shows the dependence of the degree of conversion in the polyion coupling reaction for the mixture of cetylpyridinium bromide and polyethylene oxide-block-polymethacrylic acid.

DETAILED DESCRIPTION OF THE INVENTION

Filed concurrently with this application is an application entitled "COMPOSITIONS FOR DELIVERY OF BIOLOGICAL AGENTS", Ser. No. 60/049,552 with Alexander V. Kabanov, Adi Eisenberg and Victor A. Kabanov as the named inventors. The entire disclosure of Ser. No. 60/049,552 is hereby incorporated by reference herein.

The block copolymers used in the practice of this invention are most simply defined as conjugates of at least two different polymer segments (see, for example, Tirrel, *Interactions of Surfactants with Polymers and Proteins*. Goddard and Ananthapadmanabhan, Eds., pp. 59 et seq., CRC Press (1992)). Some block copolymer architectures are presented below:

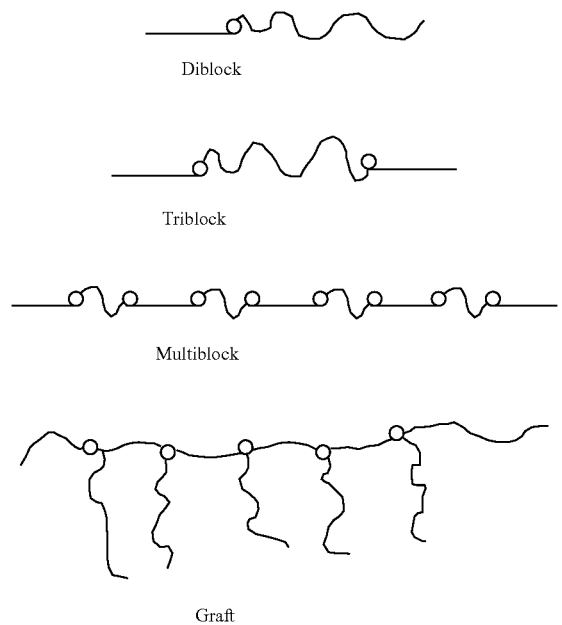

Diblock

Triblock

Multiblock

Graft

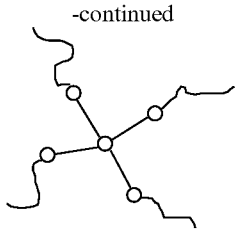

(AB)$_n$ Starblock

A$_4$B$_2$ Starblock

The simplest block copolymer architecture contains two segments joined at their termini to give an A-B type diblock. Consequent conjugation of more than two segments by their termini yields A-B-A type triblock, . . . ABAB . . . type multiblock, or even multisegment . . . ABC . . . architectures. If a main chain in the block copolymer can be defined in which one or several repeating units are linked to different polymer segments, then the copolymer have a graft architecture, e.g. A(B)$_n$ type. More complex architectures include for example (AB)$_n$ or A$_n$B$_m$ starblocks that have more than two polymer segments linked to a single center.

One method to produce block copolymers includes anionic polymerization with sequential addition of two monomers (see, for example, Schmolka, *J. Am. Oil Chem. Soc.* 1977, 54: 110; Wilczek-Vera et al., *Macromolecules* 1996, 29: 4036). This technique yields block copolymers with a narrow molecular mass distribution of the polymeric segments. Solid-phase synthesis of block copolymers has been developed recently that permit controlling the growth of the polymer segments with very high precision (Vinogradov et al., *Bioconjugate Chemistry* 1996, 7: 3). In some cases the block copolymers are synthesized by initiating polymerization of a polymer segment on ends of another polymer segment (Katayose and Kataoka, *Proc. Intern. Symp. Control. Rel. Bioact. Materials,* 1996, 23: 899) or by conjugation of complete polymer segments (Kabanov et al., *Bioconjugate Chem.* 1995, 6: 639; Wolfert et al., *Human Gene Ther.* 1996, 7: 2123). Properties of block copolymers in relation to this invention are determined by (1) block copolymer architecture and (2) properties of the polymer segments. They are independent of the chemical structure of the links used for conjugation of these segments (see, for example, Tirrel, supra; Sperling, *Introduction to Physical Polymer Science,* 2d edn., p. 46 et seq., John Wiley & Sons (1993)).

In one preferred embodiment the block copolymer is selected from the group consisting of polymers of formulas N—P, (P—N)$_n$—P, N—(P—N), N—(P—N)$_n$—P wherein N is a nonionic, water soluble segment ("N-type segment"), P is polyionic segment ("P-type segment") and n is an integer from 1 to 5000. It is preferred that the degrees of polymerization of N-type and P-type segments are from about 3 to about 50000, more preferably from about 5 to about 5000, still more preferably from about 20 to about 500. If more than one segment of the same type comprise one block copolymer, then these segments may all have the same lengths or may have different lengths.

The preferred polyanion P-type segments include, but are not limited to those such as polymethacrylic acid and its salts, polyacrylic acid and its salts, copolymers of methacrylic acid and its salts, copolymers of acrylic acid and its salts, heparin, poly(phosphate), polyamino acid (e.g. polyaspartic acid, polyglutamic acid, and their copolymers containing a plurality of anionic units), polymalic acid, polylactic acid, polynucleotides, carboxylated dextran, and the like. Particularly preferred polyanion P-type segments are the products of polymerization or copolymerization of monomers which polymerize to yield a product having carboxyl pendant groups. Representative examples of such monomers include acrylic acid, aspartic acid 1,4-phenylenediacrylic acid, citraconic acid, citraconic anhydride, trans-cinnamic acid, 4-hydroxy-3-methoxy cinnamic acid, p-hydroxy cinnamic acid, trans-glutaconic acid, glutamic acid, itaconic acid, linoleic acid, linolenic acid, methacrylic acid, maleic acid, maleic anhydride, mesaconic acid, trans-β-hydromuconic acid, trans—trans muconic acid, oleic acid, ricinoleic acid, 2-propene-1-sulfonic acid, 4-styrene sulfonic acid, trans-traumatic acid, vinylsulfonic acid, vinyl phosphonic acid, vinyl benzoic acid and vinyl glycolic acid.

Preferred polycation P-type segments include but are not limited to polyamino acid (e.g., polylysine), alkanolamine esters of polymethacrylic acid (e.g., poly-(dimethylammonioethyl methacrylate), polyamines (e.g., spermine, polyspermine, polyethyleneimine), polyvinyl pyridine, and the quaternary ammonium salts of said polycation segments.

It is preferred to use nontoxic and non-immunogenic polymer-forming N-type and P-type segments. Because of elevated toxicity and immunogenicity of cationic peptides the non-peptide P-type segments are particularly preferred.

In the case of block copolymers having at least one polyanionic segment, the nonionic segment may include, without limitation, polyetherglycols (e.g. poly(ethylene oxide), poly(propylene oxide)) copolymers of ethylene oxide and propylene oxide, polysaccharides (e.g. dextran), products of polymerization of vinyl monomers (e.g., polyacrylamide, polyacrylic esters (e.g., polyacroloyl morpholine), polymethacrylamide, poly(N-2-hydroxypropyl) methacrylamide, polyvinyl alcohol, polyvinyl pyrrolidone, polyvinyltriazole, N-oxide of polyvinylpyridine), polyortho esters, polyamino acids, polyglycerols (e.g., poly-2-methyl-2-oxazoline, poly-2-ethyl-2-oxazoline) and copolymers and derivatives thereof.

Block copolymers comprising at least one polycationic segment may be similarly formulated using nonionic segments such as polyetherglycols (e.g., polyethylene glycol) or copolymers of ethylene oxide and propylene oxide. See, for example, Bronstein et al., Proc. Am. Chem. Soc., Division of Polymeric Materials: Science and Engineering, 76: 52 (1997); Kabanov et al., U.S. Pat. No. 5,656,611; Spatz et al., Macromolecules, 29: 3220 (1996); Wolfert et al., Human Gene Ther., 7: 2123 (1996); Harada and Kataoka, Macromolecules, 29: 3220 (1996).

The term surfactant is used herein in a most general sense to encompass any surface active agent that is adsorbed at interface (see, for example, Martin, *Physical Pharmacy*, 4th edn., p. 370 et seq., Lea & Febiger, Philadelphia, London, 1993). These surface active agents in particular decrease the surface tension at the air-water interface in aqueous solutions (see, for example, Martin, *Physical Pharmacy*, 4th edn., p. 370 et seq., Lea & Febiger, Philadelphia, London, 1993) and include without limitation micelle forming amphiphiles, soaps, lipids, surface active drugs and other surface active biological agents, and the like (see, for example, Martin, *Physical Pharmacy*, 4th edn., Lea & Febiger, Philadelphia, London, 1993; Marcel Dekker, New York, Basel, 1979; Atwood and Florence, *J. Pharm. Pharmacol.* 1971, 23: 242S; Atwood and Florence, *J. Pharm. Sci.* 1974, 63: 988; Florence and Attwood, *Physicochemical Principles of Pharmacy*, 2nd edn., p. 180 et seq., Chapman and Hall, New York, 1988; Hunter, *Introduction to Modern Colloid Science, p.* 12 et seq., Oxford University Press, Oxford, 1993). The term cationic surfactant is used herein to encompass, without limitation any surfactant that can produce cation groups in aqueous solution. This includes, without limitation strong bases (e.g., quaternary ammonium or pyridinium salts, and the like) that dissociate in aqueous solution to form cationic groups and relatively weak bases (e.g., primary amines, secondary amines, and the like) that protonate in aqueous solution to produce a cationic group as a result of an acidic-basic reaction. Similarly, the term anionic surfactant is used herein to encompass, without limitation any surfactant that can produce anionic groups in aqueous solution. This includes, without limitation strong acids and their salts (e.g., akylsulfates, alkylsulfonates, alkylphosphonates, and the like) that dissociate in aqueous solution to form anionic groups and weak acids (e.g., carboxylic acids) that ionize in aqueous solution to produce an anionic group as a result of an acidic-basic reaction.

The charged surfactants that may be used in the practice of this invention are broadly characterized as cationic and anionic surfactants having hydrophobic/lipophilic groups, i.e., the groups poorly soluble in water, and/or revealing an ability to adsorb at water-air interface, and/or solubilize in organic solvents with low polarity and/or self-assemble in aqueous media to form a nonpolar microphase. The use of such compounds in an important feature of this invention. The interactions of hydrophobic groups of surfactant molecules with each other contribute to cooperative stabilization of the ionic complexes between the block copolymers and surfactants of the opposite charge in the compositions of the current invention, as will be further described below. Typically, the cationic surfactants will be lipophilic quaternary ammonium salts, lipopolyamines, lipophilic polyamino acids or a mixture thereof, particularly those proposed heretofore as a constituent of cationic lipid formulations for use in gene delivery. Various examples of classes and species of suitable cationic surfactants are provided hereinbelow.

Cationic surfactants that can be used in the compositions of the invention include, but are not limited to primary amines (e.g., hexylamine, heptylamine, octylamine, decylamine, undecylamine, dodecylamine, pentadecyl amine, hexadecyl amine, oleylamine, stearylamine, diaminopropane, diaminobutane, diaminopentane, diaminohexane, diaminoheptane, diaminooctane, diaminononane, diaminodecane, diaminododecane), secondary amines (e.g., N,N-distearylamine, adrenolutin, adrenalone, adrenolglomerulotropin, albuterol, azacosterol, benzoctamine, benzydamine, carazolol, cetamolol, spirogermanium), tertiary amines (e.g., N,N',N'-polyoxyethylene(10)-N-tallow-1, 3-diaminopropan e, acecainide, adiphenine hydrochloride, adinozalam, ahistan, alloclamide, allocryptopyne, almitrine, amitriptyline, anileridine, aprindine, bencyclane, benoxinate, biphenamine, brompheniramine, bucumolol, bufetolol, bufotenine, bufuralol, bunaftine, bunitrolol, bupranolol, butacaine, butamirate, butethamate, butofilolol, butoxycaine, butriptyline, captodiamine, caramiphen hydrochloride, carbetapentane, carbinoxamine, carteolol, cassaidine, cassaine, cassamine, chlorpromazine, dimenoxadol, dimethazan, diphehydramine, orphenandrine, pyrilamine, pyrisuccidianol, succinylcholone iodide, tetracaine, and the like), quaternary ammonium salts, which include aromatic and non-aromatic ring-containing compounds (e.g. dodecyltrimethylammonium bromide, hexadecyltrimethylammonium bromide, alkyltrimethylammonium bromide, tetradecyltrimethylammonium bromide, benzalkonium chloride, benzethonium chloride, benzoquinonium chloride, benzoxonium chloride, bibenzonium bromide, cetalkonium chloride, cethexonium bromide, benzylonium bromide, benzyldimethyldodecylammonium chloride, benzyldimethylhexadecylammonium chloride, benzyltrimethylammonium methoxide, cetyldimethylethylammonium bromide, dimethyldioctadecyl ammonium bromide (DDAB) (see, e.g., Whitt et al., Focus, 1991, 13: 8), methylbenzethonium chloride, decamethonium chloride, methyl mixed trialkyl ammonium chloride, methyl trioctylammonium chloride, N-alkyl pyridinium salts, N-alkylpiperidinium salts, quinaldinium salts, amprolium, benzylpyrinium, bisdequalinium halides, azonium and azolium salts such as anisotropine methylbromide, butropium bromide, N-butylscopolammonium bromide, tetrazolium blue, quinolinium derivatives (such as atracurium besylate), piperidinium salts, such as bevonium methyl sulfate and thiazolium salts, such as beclotiamine), 1,2-diacyl-3-(trimethylammonio)propane (acyl group=dimyristoyl, dipalmitoyl, distearoyl, dioleoyl), 1,2-diacyl-3-(dimethylammonio)propane (acyl group=dimyristoyl, dipalmitoyl, distearoyl, dioleoyl), 1,2-dioleoyl-3-(4'-trimethylammonio) butanoyl-sn-glycerol, 1,2-dioleoyl-3-succinyl-sn-glycerol choline ester, cholesteryl (4'-trimethylammonio) butanoate), heterocyclic amines (e.g., azacuclonol, azaperone, azatadine, benzetimide, benziperylon, benzylmorphine, bepridil, biperidene, budipine, buphanamine, buphanitine, butaperazine, butorphanol, buzepide, calycanthine, carpipramine), imidazoles (e.g., azanidazole, azathiopropine, bifonazole, bizantrene, butacanazole, cafaminol), triasoles (e.g., bitertanol), tetrazoles (e.g., azosemide), phenothiazines (e.g., azures A, B, C), aminoglycans (e.g., daunorubicin, doxorubicin, carminomycin, 4'-epiadriamycin, 4-demethoxy-daunomycin, 11-deoxy-daunorubicin, 13-deoxydaunorubicin, adriamycin-14-benzoate, adriamycin-14-actanoate, adriamycin-14-naphthaleneacetate), rhodamines (e.g. rhodamine 123), acridines (e.g. acranil, acriflavine, acrisorcin), dicationic bolaform electrolytes (C12Me6; C12Bu6), dialkylglycetylphosphorylcholine, lysolecithin), cholesterol hemisuccinate choline ester, lipopolyamines (e.g., dioctadecylamidoglycylspermine (DOGS), dipalmitoyl phosphatidylethanolamidospermine (DPPES), N'-octadecylsperminecarboxamide hydroxytrifluoroacetate, N',N''-dioctadecylspermine-carboxamide hydroxytrifluoroacetate, N'-nonafluoropentadecylosperminecarboxamide hydroxytrifluoroacetate, N',N''-dioctyl (sperminecarbonyl)glycinamide hydroxytrifluoroacetate, N'-(heptadecafluorodecyl)-N'-(nonafluoropentadecyl)-sperminecarbonyl)glycinamede hydroxytrifluoroacetate, N'-[3,6,9-trioxa-7-(2'-oxaeicos-11'-enyl)heptaeicos-18-enyl]sperminecarboxamide hydroxytrifluoroacetate, N'-(1,2-dioleoyl-sn-glycero-3-phosphoethanoyl)spermine carboxamide hydroxytrifluoroacetate) (see, for example, Behr et. al., Proc. Natl. Acad. Sci. 1989, 86: 6982; Remy et al., Bioconjugate Chem. 1994, 5: 647), 2,3-dioleyloxy-N-[2(spermine-carboxamido) ethyl]-N,N-dimethyl-1-propanaminiumtrifluoroacetate (DOSPA) (see, for example, Ciccarone et al., Focus 1993, 15: 80), N,N$_I$, N$_{II}$, N$_{III}$-tetramethyl-N,N$_I$, N$_{II}$, N$_{III}$-tetrapalmitylspermine (TM-TPS) (Lukow et al., J. Virol. 1993, 67:4566), N-[1-(2,3-dioleyloxy)propyl]-N,N,N-trimethylamonium chloride (DOTMA) (see, for example, Felgner, et al., Proc. Natl. Acad. Sci. USA 1987, 84: 7413; Ciccarone et al., Focus 1993, 15: 80), 1,2-dioleoyl-3-dimethyl-hydroxyethyl ammonium bromide (DORI) (see, for example, Felgner et al., J. Biol. Chem. 1994, 269:2550), 1,2-dioleyloxypropyl-3-dimethyl-hydroxyethyl ammonium bromide (DORIE) (see, for example, Felgner et al., J. Biol. Chem. 1994, 269: 2550), 1,2-dioleyloxypropyl-3-dimethyl-hydroxypropyl ammonium bromide (DORIE-HP) (see, for example, Felgner et al., J. Biol. Chem. 1994, 269:2550), 1,2-dioleyloxypropyl-3-dimethyl-hydroxybutyl ammonium bromide (DORIE-HB) (see, for example, Felgner et al., J. Biol. Chem. 1994, 269: 2550), 1,2-dioleyloxypropyl-3-dimethyl-hydroxypentyl ammonium bromide (DORIE-HPe) (see, for example, Felgner et al., J. Biol. Chem. 1994, 269: 2550), 1,2-dimyristyloxypropyl-3-dimethyl-hydroxyethyl ammonium bromide (DMRIE) (see, for example, Felgner et al., J. Biol. Chem. 1994, 269: 2550), 1,2-dipalmitoyloxypropyl-3-dimethyl-hydroxyethyl ammonium bromide (DPRIE) (see, for example, Felgner et al., J. Biol. Chem. 1994, 269: 2550), 1,2-distearoyloxypropyl-3-dimethyl-hydroxyethyl ammonium bromide (DSRIE) (see, for example, Felgner et al., J. Biol. Chem. 1994, 269: 2550), N,N-dimethyl-N-[2-(2-methyl-4-(1,1,3,3-tetramethylbuty l)-phenoxy]ethoxy)ethyl]-benzenemethanaminium chloride (DEBDA), N-[1-(2,3-dioleyloxy)propyl]-N,N,N,-trimethylammonium methylsulfate (DOTAB), lipopoly-L(or D)-lysine (see, for example, Zhou, et al., Biochim. Biophys. Acta 1991, 1065: 8), poly(L (or D)-lysine conjugated to N-glutarylphosphatidylethanolamine lysine (see, for example, Zhou, et al., Biochim. Biophys. Acta 1991, 1065:8), didodecyl glutamate ester with pendant amino group ($C_{12}GluPhC_nN^+$) (see, for example, Behr, Bioconjugate Chem. 1994, 5: 382), ditetradecyl glutamate ester with pendant amino group ($C_{14}GluC_nN^+$) (see, foe example, Behr, Bioconjugate Chem. 1994, 5: 382), 9-(N',N''-dioctadecylglycinamido) acridine (see, for example, Remy et al., Bioconjugate Chem. 1994, 5: 647), ethyl 4-[[N-[3-bis (octadecylcarbamoyl)-2-oxapropylcarbonyl]glycinamido]p yrrole-2-carboxamido]-4-pyrrole-2-carboxylate (see, for example, Remy et al., Bioconjugate Chem. 1994, 5: 647), N',N'-dioctadecylornithylglycinamide hydroptrifluoroacetate (see, for example, Remy et al., Bioconjugate Chem. 1994, 5: 647), cationic derivatives of cholesterol (e.g., cholesteryl-3(-oxysuccinamidoethylenetrimethylammonium salt, cholesteryl-3(-oxysuccinamidoethylenedimethylamine, cholesteryl-3(-carboxyamidoethylenetrimethylammonium salt, cholesteryl-3(-carboxyamidoethylenedi-methylamine, 3([N-(N',N'-dimethylaminoetanecarbomoyl]cholesterol) (see, for example, Singhal and Huang, In Gene Therapeutics, Wolff, Ed., p. 118 et seq., Birkhauser, Boston, 1993), pH-sensitive cationic lipids (e.g., 4-(2,3-bis-palmitoyloxy-propyl)-1-methyl-1H-imidazole, 4-(2,3-bis-oleoyloxy-propyl)-1-methyl-1H-imidazole, cholesterol-(3-imidazol-1-yl propyl) carbamate, 2,3-bis-palmitoyl-propyl-pyridin-4-yl-amine) and the like (see, for example, Budker et al., Nature Biotechnology 1996, 14: 760).

Especially useful in the context of gene delivery and other applications are compositions comprising mixtures of cationic surfactant and nonionic sufactants including, but not limited to dioloeoyl phosphatidylethanolamine (DOPE), dioleoyl phosphatidylcholine (DOPC) (see, for example, Felgner, et al., Proc. Natl. Acad. Sci. USA 1987; Singhal and Huang, In Gene Therapeutics, Wolff, Ed., p. 118 et seq., Birkhauser, Boston, 1993). This includes, in particular, commercially available cationic lipid compositions including but not limited to LipofectAMINE™, Lipofectine®, DMRIE-C, CellFICTIN™, LipofectACE™, Transfectam reagents (see, for example, Ciccarone et al., *Focus* 1993, 15: 80; Lukow et al., *J. Virol.* 1993, 67: 4566; Behr, *Bioconjugate Chem.* 1994, 5: 382; Singhal and Huang, In *Gene Therapeutics*, Wolff, Ed., p. 118 et seq., Birkhauser, Boston, 1993; GIBCO-BRL Co.; Promega Co., Sigma Co) and other cationic lipid compositions used for transfection of cells (see, for example, Felgner et al., *J. Biol. Chem.* 1994, 269: 2550; Budker et al., supra.

The anionic surfactants that can be used in the compositions of the present invention include, but are not limited to alkyl sulfates, alkyl sulfonates, fatty acid soaps, including salts of saturated and unsaturated fatty acids and derivatives (e.g., adrenic acid, arachidonic acid, 5,6-dehydroarachidonic acid, 20-hydroxyarachidonic acid, 20-trifluoro arachidonic acid, docosahexaenoic acid, docosapentaenoic acid, docosatrienoic acid, eicosadienoic acid, 7,7-dimethyl-5,8-eicosadienoic acid, 7,7-dimethyl-5,8-eicosadienoic acid, 8,11-eicosadiynoic acid, eicosapentaenoic acid, eicosatetraynoic acid, eicosatrienoic acid, eicosatriynoic acid, eladic acid, isolinoleic acid, linoelaidic acid, linoleic acid, linolenic acid, dihomo-γ-linolenic acid, γ-linolenic acid, 17-octadecynoic acid, oleic acid, phytanic acid, stearidonic acid, 2-octenoic acid, octanoic acid, nonanoic acid, decanoic acid, undecanoic acid, unde celenic acid, lauric acid, myristoleic acid, myristic acid, palmitic acid, palmitoleic acid, heptadecanoic acid, stearic acid, nonanedecanoic acid, heneicosanoic acid, docasanoic acid, tricosanoic acid, tetracosanoic acid, cis-15-tetracosenoic acid, hexacosanoic acid, heptacosanoic acid, octacosanoic acid, triocantanoic acid), salts of hydroxy-, hydroperoxy-, polyhydroxy-, epoxy-fatty acids (see, for example, Ingram and Brash, *Lipids* 1988, 23:340; Honn et al., *Prostaglandins* 1992, 44: 413; Yamamoto, *Free Radic. Biol. Med.* 1991, 10: 149; Fitzpatrick and Murphy, *Pharmacol. Rev.* 1989, 40: 229; Muller et al., *Prostaglandins* 1989, 38:635; Falgueyret et al., *FEBS Lett.* 1990, 262: 197; Cayman Chemical Co., 1994 Catalog, pp. 78–108), salts of saturated and unsaturated, mono- and poly-carboxylic acids (e.g., valeric acid, trans-2,4-pentadienoic acid, hexanoic acid, trans-2-hexenoic acid, trans-3-hexenoic acid, 2,6-heptadienoic acid, 6-heptenoic acid, heptanoic acid, pimelic acid, suberic acid, sebacicic acid, azelaic acid, undecanedioic acid, decanedicarboxylic acid, undecanedicarboxylic acid, dodecanedicarboxylic acid, hexadecanedioic acid, docasenedioic acid, tetracosanedioic acid, agaricic acid, aleuritic acid, azafrin, bendazac, benfurodil hemisuccinate, benzylpenicillinic acid, p-(benzylsulfonamido)benzoic acid, biliverdine, bongkrekic acid, bumadizon, caffeic acid, calcium 2-ethylbutanoate, capobenic acid, carprofen, cefodizime, cefinenoxime, cefixime, cefazedone, cefatrizine, cefamandole, cefoperazone, ceforanide, cefotaxime, cefotetan, cefonicid, cefotiam, cefoxitin, cephamycins, cetiridine, cetraric acid, cetraxate, chaulmoorgic acid, chlorambucil, indomethacin, protoporphyrin IX, protizinic acid), prostanoic acid and its derivatives (e.g., prostaglandins) (see, for example, Nelson et al., *C&EN* 1982, 30–44; Frolich, *Prostaglandins,* 1984, 27: 349; Cayman Chemical Co., 1994 Catalog, pp. 26–61), leukotrienes and lipoxines (see for example, Samuelsson et al., *Science* 1987, 237: 1171; Cayman Chemical Co., 1994 Catalog, pp. 64–75), alkyl phosphates, O-phosphates (e.g., benfotiamine), alkyl phosphonates, natural and synthetic lipids (e.g., dimethylallyl pyrophosphate ammonium salt, S-farnesylthioacetic acid, farnesyl pyrophosphate, 2-hydroxymyristic acid, 2-fluorpalmitic acid, inositoltrphosphates, geranyl pyrophosphate, geranygeranyl pyrophosphate, α-hydroxyfarnesyl phosphonic acid, isopentyl pyrophoshate, phosphatidylserines, cardiolipines, phosphatidic acid and derivatives, lysophosphatidic acids, sphingolipids and the like), synthetic analogs of lipids such as sodium-dialkyl sulfosuccinate (e.g., Aerosol OT®), n-alkyl ethoxylated sulfates, n-alkyl monothiocarbonates, alkyl- and arylsulfates (asaprol, azosulfamide, p-(benzylsulfonamideo)benzoic acid, cefonicid, CHAPS), mono- and dialkyl dithiophosphates, N-alkanoyl-N-methylglucamine, perfluoroalcanoate, cholate and desoxycholate salts of bile acids, 4-chlorindoleacetic acid, cucurbic acid, jasmonic acid, 7-epi jasmonic acid, 12-oxo phytodienoic acid, traumatic acid, tuberonic acid, abscisic acid, acitertin, and the like.

The preferred cationic and anionic surfactants of this invention also include fluorocarbon and mixed fluorocarbon-hydrocarbon surfactants. See, for example, Mukerjee, P. *Coll. Surfaces A: Physicochem. Engin. Asp.* 1994, 84: 1; Guo et al., *J. Phys. Chem.* 1991, 95: 1829; Guo et al., *J. Phys. Chem.,* 1992, 96: 10068. The list of such surfactants that are useful in the present invention includes, but is not limited to the salts of perfluoromonocarboxylic acids (e.g., pentafluoropropionic acid, heptafluorobutyric acid, nonanfluoropentanoic acid, tridecafluoroheptanoic acid, pentadecafluorooctanoic acid, heptadecafluorononanoic acid, nonadecafluorodecanoic acid, perfluorododecanoic acid, perfluoropolycarboxylic acids, perfluorotetradecanoic acid) and the salts of perfluoro-polycarboxylic acids (e.g., hexafluoroglutaric acid, perfluoroadipic acid, perfluorosuberic acid, perfluorosebacic acid), double tail hybrid surfactants, $(C_mF_{2m+1})$ $(C_nH_{2n+1})CH—OSO_3Na$ (see, for example, Guo et al., *J. Phys. Chem.,* 1992, 96: 6738, Guo et al., *J. Phys. Chem.* 1992, 96: 10068; Guo et al., *J. Phys. Chem.,* 1992, 96: 10068), fluoroaliphatic phosphonates, fluoroaliphatic sulphates, and the like.

The biological agent compositions of this invention may additionally contain nonionic or zwitterionic surfactants including but not limited to phosholipids (e.g. phosphatidylethanolamines, phosphatidylglycerols, phosphatidylinositols, diacyl phosphatidylcholines, di-O-alkyl phosphatidylcholines, platelet-activating factors, PAF agonists and PAF antagonists, lysophosphatidylcholines, lysophosphatidylethanol-amines, lysophosphatidylglycerols, lysophosphatidylinositols, lyso-platelet-activating factors and analogs, and the like), saturated and unsaturated fatty acid derivatives (e.g., ethyl esters, propyl esters, cholesteryl esters, coenzyme A esters, nitrophenyl esters, naphtyl esters, monoglycerids, diglycerids, and triglycerids, fatty alcohols, fatty alcohol acetates, and the like), lipopolysaccharides, glyco- and shpingolipids (e.g. ceramides, cerebrosides, galactosyldiglycerids, gangliosides, lactocerebrosides, lysosulfatides, psychosines, shpingomyelins, sphingosines, sulfatides), chromophoric lipids (neutral lipids, phospholipids, cerebrosides, sphingomyelins), cholesterol and cholesterol derivatives, Amphotericin B, abamectin, acediasulfone, n-alkylphenyl polyoxyethylene ether, n-alkyl polyoxyethylene ethers (e.g., Triton™), sorbitan esters (e.g. Span™), polyglycol ether surfactants (Tergitol™), polyoxyethylene-sorbitan (e.g., Tween™), polysorbates, polyoxyethylated glycol monoethers (e.g., Brij™, polyoxylethylene 9 lauryl ether, polyoxylethylene 10 ether, polyoxylethylene 10 tridecyl ether), lubrol, copolymers of ethylene oxide and propylene oxide (e.g., Pluronic™, Pluronic R™, Teronic™, Pluradot™, alkyl aryl polyether alcohol (Tyloxapol™), perfluoroalkyl polyoxylated amides, N,N-bis[3-D-gluconamidopropyl]cholamide, decanoyl-N-methylglucamide, n-decyl α-D-glucopyranozide, n-decyl β-D-glucopyranozide, n-decyl β-D-maltopyranozide, n-dodecyl β-D-glucopyranozide, n-undecyl β-D-glucopyranozide, n-heptyl (-d-glucopyranozide, n-heptyl β-D-thioglucopyranozide, n-hexyl β-D-glucopyranozide, n-nonanoyl β-D-glucopyranozide 1-monooleyl-rac-glycerol, nonanoyl-N-methylglucamide, n-dodecyl α-D-maltoside, n-dodecyl β-D-maltoside, N,N-bis[3-gluconamidepropyl]deoxycholamide, diethylene glycol monopentyl ether, digitonin, heptanoyl-N-methylglucamide, heptanoyl-N-methylglucamide, octanoyl-N-methylglucamide, n-octyl β-D-glucopyranozide, n-octyl α-D-glucopyranozide, n-octyl β-D-thiogalactopyranozide, n-octyl β-D-thioglucopyranozide, betaine $(R_1R_2R_3N^+R'CO_2^-$, where $R_1R_2R_3R'$ hydrocarbon chains), sulfobetaine $(R_1R_2R_3N^+R'SO_3^-)$, phoshoplipids (e.g. dialkyl phosphatidylcholine), 3-[(3-cholamidopropyl)-dimethylammonio]-2-hydroxy-1-propanesulfonate, 3-[(3-cholamidopropyl)-dimethylammonio]-1-propanesulfonate, N-decyl-N,N-dimethyl-3-ammonio-1-propanesulfonate, N-dodecyl-N,N-dimethyl-3-ammonio-1-propanesulfonate, N-hexadecyl-N,N-dimethyl-3-ammonio-1-propanesulfonate, N-octadecyl-N,N-dimethyl-3-ammonio-1-propanesulfonate, N-octyl-N,N-dimethyl-3-ammonio-1-propanesulfonate, N-tetradecyl-N,N-dimethyl-3-ammonio-1-propanesulfonate, dialkyl phoshatitidylethanolamine.

Surface active biological agents that may be used in the practice of this invention include those having utility in diagnostics or imaging, as well as those capable of acting on a cell, organ or organism to create a change in the functioning of the cell, organ or organism, including but not limited to pharmaceutical agents. Such biological agents include a wide variety of substances that are used in diagnostics, therapy, immunization or otherwise are applied to combat human and animal disease. Such agents include but are not limited to analgesic agents, anti-inflamatory agents, antibacterial agents, antiviral agents, antifungal agents, antiparasitic agents, tumoricidal or anti-cancer agents, toxins, hormones, neurotransmitters, immunomodulators, dyes, radiolabels, radio-opaque compounds, fluorescent compounds, cell receptor binding molecules, anti-glaucomic agents, mydriatic compounds and local anesthetics.

It is essential that the biological agents of this invention are charged, to form the complex with the block copolymer of the opposite charge. The term charged biological agent is used herein to encompass, without limitation any biological agent that can produce either cation or anion groups in aqueous solution. This includes, without limitation strong bases (e.g., quaternary ammonium or pyridinium salts, and the like) that dissociate in aqueous solution to form cationic group, and weak bases (e.g., primary amines, secondary amines, and the like) that protonate in aqueous solution to produce a cationic group as a result of an acidic-basic reaction. The anionic biological agents include without limitation strong acids and their salts (e.g., agents containing sulfate groups, sulfonate groups, phosphate groups, phosphonate groups and the like) that dissociate in aqueous solution to form anionic group, and weak acids (e.g., carboxylic acids) that ionize in aqueous solution to produce an anionic group as a result of an acidic-basic reaction.

The biological agents which may be used in the compositions of the invention may include, but are not limited to non-steroidal anti-inflamatories, such as indomethacin, salicylic acid acetate, ibuprofen, sulindac, piroxicam, and naproxen, antiglaucomic agents such as timolol or pilocarpine, neurotransmitters such as acetylcholine, anesthetics such as dibucaine, neuroleptics such as the phenothiazines (e.g., compazine, thorazine, promazine, chlorpromazine, acepromazine, aminopromazine, perazine, prochlorperazine, trifluoperazine, and thioproperazine), rauwolfia alkaloids (e.g., resperine and deserpine), thioxanthenes (e.g., chlorprothixene and tiotixene), butyrophenones (e.g., haloperidol, moperone, trifluoperidol, timiperone, and droperidol), diphenylbutylpiperidines (e.g., pimozde), and benzamides (e.g., sulpiride and tiapride); tranquilizers such as glycerol derivatives (e.g., mephenesin and methocarbamol), propanediols (e.g., meprobamate), diphenylmethane derivatives (e.g., orphenadrine, benzotrapine, and hydroxyzine), and benzodiazepines (e.g., chlordiazepoxide and diazepam); hypnotics (e.g., zolpdem and butoctamide); beta-blockers (e.g., propranolol, acebutonol, metoprolol, and pindolol); antidepressants such as dibenzazepines (e.g., imipramine), dibenzocycloheptenes (e.g., amtiriptyline), and the tetracyclics (e.g., mianserine); MAO inhibitors (e.g., phenelzine, iproniazid, and selegeline); psychostimulants such as phenylehtylamine derivatives (e.g., amphetamines, dexamphetamines, fenproporex, phentermine, amfeprramone, and pemoline) and dimethylaminoethanols (e.g., clofenciclan, cyprodenate, a minorex, and mazindol); GABA-mimetics (e.g., progabide); alkaloids (e.g., codergocrine, dihydroergocristine, and vincamine); anti-Parkinsonism agents (e.g., L-dopamine and selegeline); agents utilized in the treatment of Altzheimer's disease, cholinergics (e.g., citicoline and physostigmine); vasodilators (e.g., pentoxifyline); and cerebro active agents (e.g., pyritinol and meclofenoxate).

Anti-neoplastic agents can also be used advantageously as biological agents in the compositions of the invention. Representative examples include, but are not limited to paclitaxel, daunorubicin, doxorubicin, carminomycin, 4'-epiadriamycin, 4-demethoxy-daunomycin, 11'-deoxydaunorubicin, 13-deoxydaunorubicin, adriamycin-14-benzoate, adriamycin-14-actanoate, adriamycin-14-naphthaleneacetate, vinblastine, vincristine, mitomycin C, N-methyl mitomycin C, bleomycin $A_2$, dideazatetrahydrofolic acid, aminopterin, methotrexate, cholchicine and cisplatin. Representative antibacterial agents are the aminoglycosides including gentamicin. Representative antiviral compounds are rifampicin, 3'-azido-3'-deoxythymidine (AZT), and acyclovir. Representative antifungal agents are the azoles, including fluconazole, macrolides such as amphotericin B, and candicidin.

Representative anti-parastic compounds are the antimonials. Suitable biological agents also include, without limitation vinca alkaloids, such as vincristine and vinblastine, mitomycin-type antibiotics, such as mitomycin C and N-methyl mitomycin, bleomycin-type antibiotics such as bleomycin $A_2$, antifolates such as methotrexate, aminopterin, and dideaza-tetrahydrofolic acid, taxanes, anthracycline antibiotics and others.

The compositions also can comprise enzyme inhibiting agents such as reverse transcriptase inhibitors, protease inhibitors, angiotensin converting enzymes, 5μ-reductase, and the like. Typical of these agents are peptide and non-peptide structures such as finasteride, quinapril, ramipril, lisinopril, saquinavir, ritonavir, indinavir, nelfinavir, zidovudine, zalcitabine, allophenylnorstatine, kynostatin, delaviridine, bis-tetrahydrofuran ligands (see, for example Ghosh et al., *J. Med. Chem.* 1996, 39: 3278), and didanosine. Such agents can be adminitered alone or in combination therapy; e.g., a combination therapy utilizing saquinavir, zalcitabine, and didanosine, zalcitabine, and zidovudine. See, for example, Collier et al., *Antiviral Res.* 1996, 29: 99.

Other suitable biological agents include oxygen transporters (e.g. porphines, porphirines and their complexes with metal ions), coenzymes and vitamins (e.g. NAD/NADH, vitamins B12, chlorophylls), and the like.

Suitable biological agents further include the agents used in diagnostics visualization methods, such as magnetic resonance imaging (e.g., gadolinium (III) diethylenetriamine pentaacetic acid), and may be a chelating group (e.g., diethylenetriamine pentaacetic acid, triethylenetriamine pentaacetic acid, ethylenediamine-tetraacetic acid, 1,2-diaminocyclo-hexane-N,N,N',N'-tetraaceticacid, N,N'-di(2-hydroxybenzyl) ethylene diamine), N-(2-hydroxyethyl) ethylene diamine triacetic acid and the like). Such biological agent may further include an alpha-, beta-, or gamma-emitting radionuclide (e.g., galliun 67, indium 111, technetium 99). Iodine-containing radiopaque molecules are also suitable diagnostic agents. The diagnostic agent may also include a paramagnetic or superparamagnetic element, or combination of paramagnetic element and radionuclide. The paramagnetic elements include but are not limited to gadolinium (III), dysporsium (III), holmium (III), europium (III) iron (III) or manganese (II).

The composition may further include a targeting group including but not limited to antibody, fragment of an antibody, protein ligand, polysaccharide, polynucleotide, polypeptide, low molecular mass organic molecule and the like. Such targeting group can be linked covalently to the block copolymer or surfactant, or can be non-covalently incorporated in the compositions through hydrophobic, electrostatic interactions or hydrogen bonds.

A new and unexpected finding of the present invention is that low molecular mass biological agents having from one to about five anionic groups can be formulated with block copolymers of opposite charge. The molecular masses of these biological agents are less than 4000, preferably less than 2000, still more preferably less than 700. It is further preferred that these biological agents contain a hydrophobic group providing for cooperative stabilization of the complex between the agent and block copolymer. Representative examples of biological agents that contain such a hydrophobic group include saturated and unsaturated fatty acids, arachidonic acid and derivatives, leukotrienes, porphirines, anthracycline antibiotics, prostaglandins, benzodiazepines, and the like.

While not wishing to be bound by any particular theory, it is believed that the above-described surfactants and block copolymers of opposite charge form stable complexes due to cooperative binding. (See, e.g., Goddard, In *Interactions of Surfactants with Polymers and Proteins*. Goddard and Ananthapadmanabhan, Eds., pp. 171 et seq., CRC Press, Boca Raton, Ann Arbor, London, Tokyo, 1992). Cooperative binding occurs in the sense that binding of surfactant molecules to the block copolymer is enhanced by the presence of other molecules of the same or a different surfactant already bound to the same copolymer. According to the cooperative binding mechanism which is believed to underlie this invention, surfactant binds electrostatically to the oppositely charged P-type segments of the block copolymer to form supramolecular complexes. These complexes are cooperatively stabilized by the interactions of the hydrophobic parts of surfactant molecules bound to the same P-type segment with each other. Indeed, it appears that without these hydrophobic interactions, formation of the desired complex would not occur. FIG. 1 presents the binding isotherms for interaction of cetylpyridinium bromide and dodecylpyridinium bromide with the polyethylene oxide-block-poly(sodium methacrylate) block copolymer. As can be seen in FIG. 1, a decrease in the length of the hydrophobic substituent on the surfactant, from more hydrophobic cetyl- to less hydrophobic dodecyl-, decreases the stability of the complex more than ten-fold. This binding mechanism is, in particular, characteristic for surface active biological agents. See, for example, Florence and Attwood, *Physicochemical Principles of Pharmacy,* 2nd edn., p. 180 et seq., Chapman and Hall, New York, 1988). For example, FIG. 2 provides the binding isotherms for interaction of doxorubicin and rhodamine 123 with the copolymer of polyethylene oxide-block-poly(sodium methacrylate).

Formation of the electrostatic complexes between surfactants and P-type segments results in charge neutralization. As a result hydrophobicity of the complexed segments increases and aqueous solubility decreases. However, the preferred biological agent compositions remain in the aqueous solution due to the presence of the N-type segments linked to the P-type segments. By varying the relative lengths and amounts of the N-type and P-type blocks it is possible to vary the hydrophilic-lipophilic properties of the complexes formed between the surfactant and block copolymer and to optimize the solubility of the preferred compositions. It is preferred that the compositions of the present invention are water soluble at physiological conditions (pH, osmomolarity, etc.) and temperatures. FIG. 3 shows that binding of cetylpyridinium bromide to poly(sodium methacrylate) segment alone results in formation of a water-insoluble complex, whereas binding of the same surfactant to the block copolymer polyethylene oxide-block-poly(sodium methacrylate) yields a water-soluble complex.

The compositions of the present invention normally form complexes of small size that are thermodynamically stable and do not aggregate after storing in solutions for a period of time on the order of weeks or months, depending on the type of polymer. The ability to produce particles of such limited size is important because small particles can easily penetrate into tissues through even small capillaries and enter cells via endocytosis. The preferred size of these particles is less than 500 nm, more preferred less than 200 nm, still more preferred less than 100 nm. These systems can be lyophilized and stored as a lyophilized powder and then re-dissolved to form solutions with the particles of the same size.

It is useful to consider the constituents that make up the complexes of this invention in terms of a parameter referred to herein as charge ratio of the complex. The charge ratio of the complex, herein designated as "ϕ", is the ratio of the net charge of the surfactant molecules bound with one block copolymer molecule to the net charge of the P-type segments in this block copolymer. By way of example, if the surfactant molecule has two positively charged groups and five negatively charged groups, it has a "net charge" of −3. Thus, if a surfactant with the net charge $z_1$ binds to the oppositely charged P-type segments of the block copolymer, then the charge ratio is expressed as follows:

$$\phi = \frac{n \cdot z_1}{\gamma \cdot z_2 \cdot PD} \quad (1)$$

where n is the number of surfactant molecules bound to one block copolymer molecule, $z_2$ is the net charge of the repeating unit of the P-type segment, PD is the degree of polymerization of the P-type segment, and γ is the number of P-type segments in the block copolymer molecule.

If $\phi<1$, then the complex has the same charge sign as the P-type segments; if $\phi>1$, the complex has the same charge sign as the surfactant; and if $\phi=1$, the complex is electroneutral. Therefore, by varying the molar ratio of the components in the compositions the charge of the particles formed can be changed form negative to positive and vise versa. See for example FIG. 4. As a result various biological agents can be incorporated into such particles through combination of electrostatic and hydrophobic interactions. For example, the compositions from cationic surface active biological agents (e.g., adriamycin-14-naphtaleneacetate) and anionic block copolymer (e.g., polyethylene oxide-block-poly(sodium methacrylate)) at $\phi>1$ are positively charged. The compositions from anionic surface active biological agents (e.g., indomethacin) and cationic copolymer (e.g., polyethyleneimine and polyethylene oxide) at $\phi>1$ are negatively charged.

It is further useful to introduce the parameter characterizing the ratio of the net charges of surfactant to the net charges of the P-type segments of the block copolymer in the compositions of =this invention. This parameter referred herein as composition of the mixture, and herein designated "Z" is expressed as follows:

$$Z = \frac{z_1 \cdot C_1}{\gamma \cdot z_2 \cdot PD \cdot C_2} \tag{2}$$

where $z_1$, $z_2$, $\gamma$, and PD have the same meaning as in equation (1) and $C_1$ and $C_2$ are the molar concentrations of the surfactant and block copolymer in the mixture. While not wishing to be bound to any particulate theory, it is believed that the relationship between the charge ratio of the complex and composition of the mixture is as follows, $\phi \geqq Z$ This means that $n \geqq C_1 C_2$, i.e., the number of surfactant molecules bound to one block copolymer molecule is not less that the ratio of the molar concentrations of the surfactant and copolymer in the mixture. Further, when Z is less than 1, preferably less than 0.5, $n>C_1C_2$, i.e., the number of surfactant molecules bound to one block copolymer molecule is more than the ratio of the molar concentrations of the surfactant and block copolymer in the mixture. The reason for the behavior expressed by those relationships is that the binding of surfactant molecules to the P-type segments of the block copolymer is enhanced by the presence of the molecules of surfactant already bound to the same block copolymer. Therefore, those relationships reflect the cooperative binding mechanism between the surfactant and block copolymers of the current invention.

Under certain conditions the particles of the complex spontaneously form vesicles that contain internal aqueous volume. Various biologically active agents (for example, 3'-azido-3'-deoxythymidine, water soluble protease inhibitors, interleukins, insulin and the like) can be physically entrapped into the internal aqueous volume of such vesicles. The optimal conditions for the vesicle formation is determined by the composition of the mixture, so that the vesicles form when Z is more than about 0.1 and less than 100, preferably more than 0.4 and less than 20, still more preferbly more than 0.7 less than 10.

Furthermore, the compositions of present invention can solubilize hydrophobic biological agents (e.g., paclitaxel) through nonpolar interactions in the microphase formed by the hydrophobic groups of the surfactant.

One important aspect of the current invention is that electrostatic interactions between the charged groups of the biologically active surface active agent and repeating units of the P-type segments of the block copolymer are pH-dependent. For example, FIG. 5 shows the pH-dependency of the reaction between cetylpyridinium bromide and the copolymer of polymethacrylic acid and polyethylene oxide. It is preferred that either the P-type segment of the block copolymer or the surfactant or both the P-type segment and the surfactant represent a weak acid or weak base. The preferred compositions formed are pH-dependent in the pH-range of from about pH 2.0 to about pH 10.0, more preferably in the pH-range of from about pH 3.0 to about pH 9.0, still more preferably in the pH-range of from about pH 4.0 to about pH 8.0. Dissociation of the biologically active surfactant and block copolymer complexes as a result of the pH change is characterized by step-type behavior, with more cooperative systems revealing sharper pH dependencies. Preferably these complexes dissociate when the pH change is about 3.0 units of pH, more preferably about 2.0 units of pH, still more preferably about 1.0 unit of pH. Since the biologically active surfactant and block copolymer are linked to each other through non-covalent interactions, dissociation of the complex results in the release of the biological agent. The complexes between the surfactants and block copolymers are stable in the pH range of from about pH 5.5 to about pH 8.5, preferably in the pH range of from about pH 6.5 to about pH 7.5. These complexes, however, easily dissociate when the pH shift occurs in the target tissue or cell, or other target site, which enables site-specific release of the biological agents. To facilitate for the release of the surface active biological agent from the compositions of the first embodiment the total amount of net charge of these biological agents is no more than about 5, more preferably no more than 4, still more preferably no more than 3.

The compositions of the present invention allow diverse routes of administration, including but not limited by parenteral (such as intramuscular, subcutaneous, intraperitoneal, and intraveneous), oral, topical, otic, topical, vaginal, pulmonary, and ocular. These compositions can take the form of tablets, capsules, lozenges, troches, powders, gels, syrups, elixirs, aqueous solutions, suspensions, micelles, emulsions and microemulsions.

Conventional pharmaceutical formulations are employed. In the case of tablets, for example, well-known carriers such as lactose, sodium citrate, and salts of phosphoric acid can be used. Disintegrants such as starch, and lubricating agents such as magnesium stearate, sodium lauryl sulfate and talc, as are commonly used in tablets, can be present. Capsules for oral administration can include diluents such as lactose and high molecular weight polyethylene glycols. When aqueous suspensions are required for oral use, the conjugate can be combined with emulsifying and suspending agents. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by well-known ocular delivery systems such as applicators or eyedroppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow for formation of an aerosol.

The following examples are provided to describe the invention in further detail. These examples are intended merely to illustrate specific embodiments of the compositions and methods of the invention and should in no way be construed as limiting the invention.

The ability of the biologically active compositions of the invention to alter the biological profile and activity of biological agents can be conveniently observed in a number of experimental models, as described in the following two examples.

EXAMPLE 1

The multidrug resistant KBv cell line (vinblastine resistant human epidermoid carcinoma) which express high levels of glycoprotein P (P-gp) efflux pump (Gervasoni et al., *Cancer Research,* 1991, 51: 4955) can be used to evaluate the effects of present compositions on doxorubicin cytotoxicity. KBv cells were maintained in vitro as a monolayer culture in RPMI 1640 media supplemented with 10% fetal bovine serum. The cells were cultured in the drug-free medium for minimum four passages prior to experimental use. The cells were harvested by trypsinization, plated at 2000 to 3000 cells/well in fresh medium into 96-well microtiter plates and cultured for 1 to 2 days to allow the reattachment. The doxorubicin with or without 0.02% polyethylene oxide-block-poly(sodium methacrylate) was subsequently added at various concentrations and the cell monolayers were incubated for 4 hours at 37° C. with 5% carbon dioxide. After incubation, the cell monolayers were washed three times with D-PBS and cultured for 4 days in RPMI 1640 supplemented with 10% FBS. The drug cytotoxicity was determined by a standard XTT assay (Scudievo, et al., *Cancer Research,* 1988, 48, 4827). Briefly, the sterile 1 mg/ml XTT solution in RPMI 1640 containing 5 μl/ml of 1.54 μg/ml phenazine methasulfate solution in sterile PBS was added to the cells (50 μl/well in 200 μl of medium) and incubated for 4 to 16 hours at 37° C. and 5% $CO_2$. The absorbance at λ420 was determined using a microplate reader. All the experiments were carried out in triplicates. SEM values were less than 10% ($P<0.05$). The values of IC50 were determined from the dose response curves. The results are as follows:

| Composition studied | IC50, ng/ml |
|---|---|
| Doxorubicin in assay buffer | 5 |
| Doxorubicin in 0.02% polyethylene oxide-block-poly (sodium methacrylate) | 0.1 |

The above data demonstrate that the present composition chemosensitize the multidrug resistant cancer cells with respect to MDR drug.

EXAMPLE 2

The following experiment evaluated the effects of compositions of this invention on uptake of rhodamine 123 in human intestinal epithelial cells Caco-2. These cells are expressing P-gp that controls permeability of the cells with respect to a broad class of pharmaceutical agents (Thiebault, et al. *Proc. Natl. Acad. Sci. USA* 1987, 84: 7735). Rhodamine 123 is a specific probe for the effects on the P-gp efflux system, which is commonly used for evaluation of the P-gp efflux system in cancer and normal cells (Jancis et al., *Mol. Pharmacol.* 1993, 43: 51; Lee et al., *Mol. Pharmacol.* 1994, 46: 627). From a drug delivery standpoint, blocking P-gp function in intestinal epithelial cells could have a significant impact. The Caco-2 cells were cultured in DMEM supplemented with 10% fetal bovine serum. The Caco-2 cell monolayers were grown in 24-well culture plates and used in rhodamine uptake experiments after reaching confluency. Confluency of all cell monolayers was determined by visual inspection using an inverted light microscope. 3.2 μM rhodamine 123 was formulated with 0.01% solution of the polyethylene oxide-block-poly(sodium methacrylate) in assay buffer of the following composition: NaCl (122 mM), $NaHCO_3$ (25 mM), glucose (10 mM), KCl (3 mM), $MgSO_4$ (1.2 mM), $K_2HPO_4$ (0.4 mM), $CaCl_2$ (1.4 mM) and HEPES (10 mM). The uptake of rhodamine 123 in Caco-2 cell monolayers in presence and absence of polyethylene oxide-block-poly(sodium methacrylate) was examined at 37° C. over a period of 60 minutes. After a thirty-minute per-incubation at 37° C. the assay buffer was removed and 3.2 μM rhodamine 123 with or without 0.01% polyethylene oxide-block-poly(sodium methacrylate) were added to the monolayers. These samples were exposed to the monolayers at 37° C. for 90 minutes and uptake then stopped by removing the medium and washing the Caco-2 monolayers three times with 0.5 ml ice-cold PBS. The Caco-2 monolayers were solubilized in 1.0% Triton X-100 (0.5 ml) and aliquots were removed for determining cell-associated rhodamine fluorescence and protein content. Rhodamine 123 fluorescence is determined at $\lambda_{ex}$=488 nm and $\lambda_{em}$=550 nm using Shimadzu 5000 spectrofluorimeter; and protein content is determined using the Pierce BCA method. The concentration of rhodamine 123 in the Caco-2 lyzate solution is determined by construction of standard curves. Data from the uptake studies are expressed as amount of cell-associated rhodamine/mg protein. Each data point represents the mean±SEM of 4 monolayers. The results are as follows:

| Composition studied | uptake, nmol/mg |
|---|---|
| Rhodamine 123 in assay buffer | 2.31 ± 0.48 |
| Rhodamine 123 in 0.01% polyethylene oxide-block-poly (sodium methacrylate) | 5.82 ± 1.32 |

The above data demonstrate that present composition enhances transport of MDR drug into cells expressing P-gp efflux system and that this formulation increases drug efficacy. A similar increase is observed in MDR cancer cells. Further, a similar increase is observed in hepatocytes and brain micorvessel endothelial cells suggesting that present compositions can be used effectively to deliver drugs in tumours, in liver, across intestinal barrier and blood brain barrier.

EXAMPLE 3

The effects of the present compositions on the transport of biologicaly active agents across biological barriers, such as intestinal can be conveniently demonstrated using the cell monolayers polycarbonate grown on membrane inserts. See, for example, Nerurkar et al., *Pharm Res.* 1996, 13: 528). The confluent Caco-2 monolayers grown on the polycarbonate membrane inserts were preincubated in culture media as described above. For both the preincubation period and the actual permeability experiments, 1.5 ml of media was placed on the lumenal (donor) side of the monolayer and 2.6 ml of media is placed on the ablumenal (receiver) side. The permeability of rhodamine 123 was determined by adding 3.2 μM of R123 with or without 0.01% polyethylene oxide-block-poly(sodium methacrylate) to the donor side of the Caco-2 monolayer. At various times (0–90 minutes) 100 μl samples of the receiver compartment were taken. Each sample removed was replaced with an equal volume of assay buffer. The samples were then assayed for rhodamine 123 by fluorescence spectrophotometry as described previously. To evaluate the integrity of the Caco-2 monolayers a small amount of [$^3$H]manitol (0.5 μCi/ml) will be added to the apical compartment at the start of each permeability experiment. Since manitol does not readily cross the Caco-2 monolayers, this particular marker also determines the effects of the present compositions on overall Caco-2 monolayer integrity. The data from these experiments will be analyzed by graphing the amount of rhodamine 123 that appears in the receiver solution vs. time. Each data point represents the mean±SEM of 4 monolayers. The results are as follows:

| Composition | Permeability, arb. Units | | | | |
|---|---|---|---|---|---|
| studied | 0.5 min | 15 min | 30 min | 60 min | 90 min |
| Rhodamine 123 in assay buffer | 0.004 ± 0.002 | 0.032 ± 0.003 | 0.074 ± 0.005 | 0.176 ± 0.013 | 0.264 ± 0.018 |
| Rhodamine 123 in block copolymer | 0.009 ± 0.001 | 0.040 ± 0.008 | 0.122 ± 0.033 | 0.286 ± 0.040 | 0.505 ± 0.080 |

The above data demonstrate that present composition enhances permeability of a surfactant biological agent in intestinal barrier.

Figure 1:
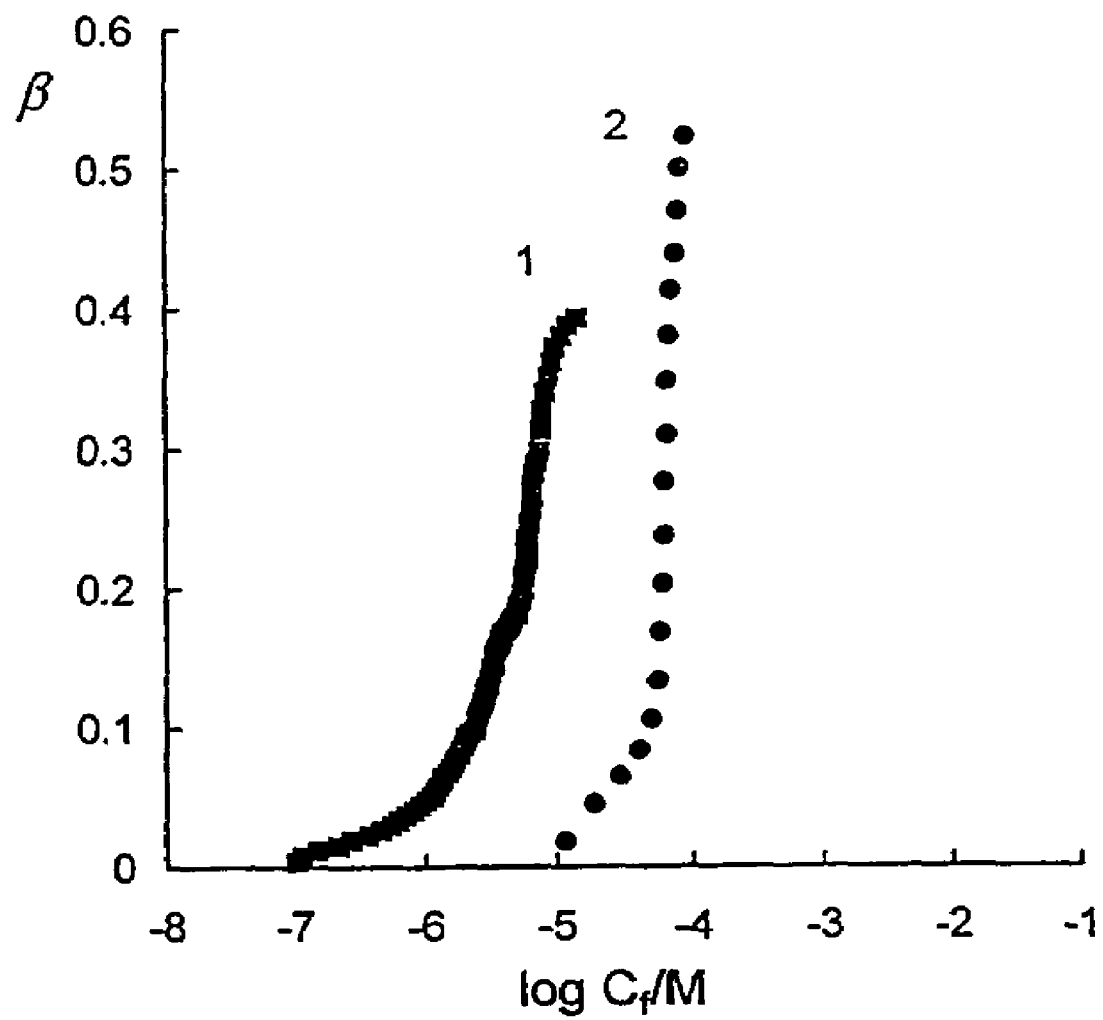
Figure 2:
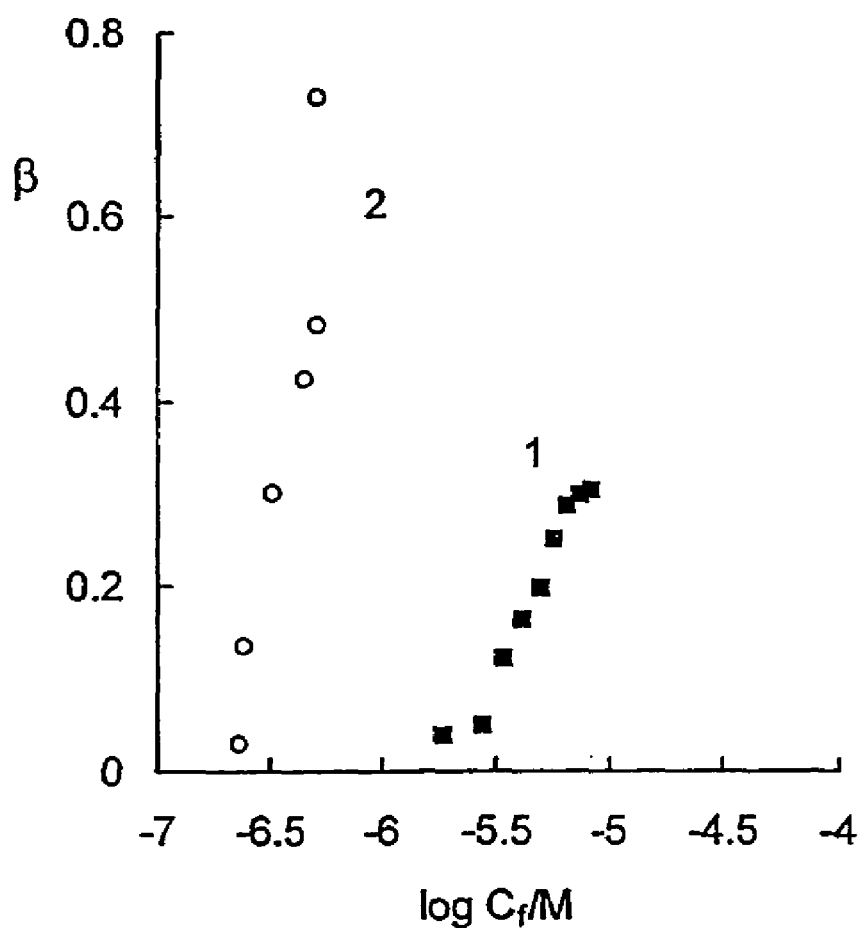
FIG. 2 is a graphical representation of binding isotherms of doxorubicin (1) and rhodamine 123 (2) to polyethylene oxide-block-poly(sodium methacrylate), in which β, a fraction of occupied binding sites, is plotted as a function of biological agent concentration.
Figure 3:
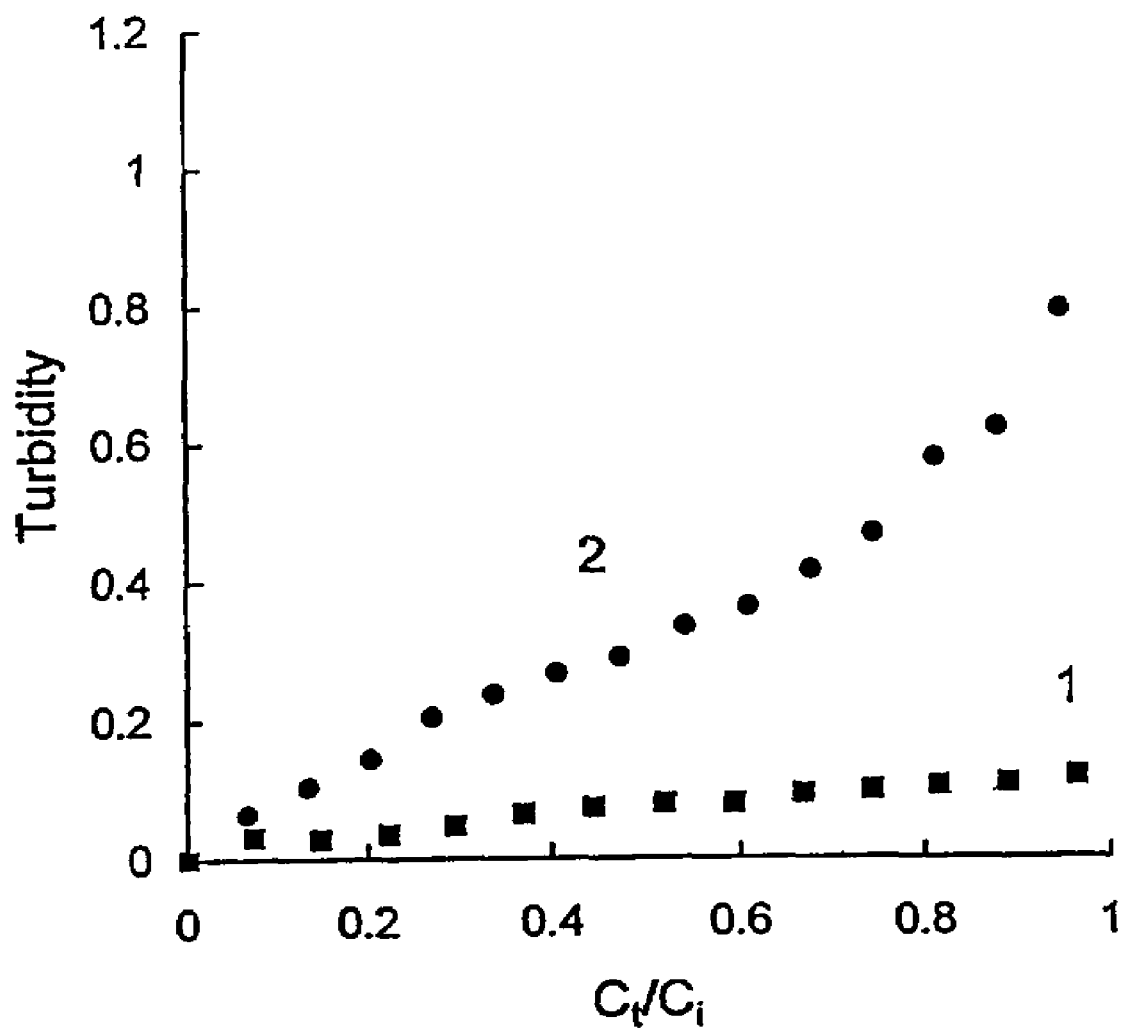
FIG. 3 is a graphical representation showing turbidity in mixtures of cetylpyridinium bromide and polyethylene oxide-block-poly(sodium methacrylate) (1) and cetylpyridinium bromide and poly(sodium methacrylate) (2), as a function of the composition of the mixture.

The following examples further illustrate the nature of this invention.

EXAMPLE 4

A. Block copolymer of tert-butyl methacrylate and ethylene oxide used in this study was prepared by sequential anionic polymerization generally following the previously published procedure (Wang et al., *J. Polym. Sci., Part A: Polym. Chem.* 1992, 30: 2251). The block lengths in copolymer were 176 for the PEO and 186 for tert-butyl methacrylate segments respectively. This copolymer was hydrolyzed to obtain the polyethylene oxide-block-polymethacrylic acid as described by Wang et al. (*J. Polym. Sci., Part A: Polym. Chem.* 1992, 30: 2251). The polyethylene oxide-block-poly (sodium methacrylate) was prepared by redissolving the acid form of the copolymer in tetrahydrofurane:methanol mixture (95:5 v/v) and adding NaOH in methanol. The precipitate containing polyethylene oxide-block-poly(sodium methacrylate) was filtered and washed with methanol, then redissolved in water and freeze dried. The concentration of carboxylate groups in the copolymer sample was estimated by potentiometric titration.

B. The binding isotherms of cetylpyridinium bromide (Sigma Co.) and dodecylpyridinium bromide (Sigma Co.) with the polyethylene oxide-block-poly(sodium methacrylate) copolymer were determined potentiometrically by using the following ion-selective electrode: Ag/AgCl|1 M $NH_4NO_3$ agar bridge|reference solution (surfactant, $2.5 \cdot 10^{-4}$ M)|PVC membrane|sample solution|1 M $NH_4NO_3$ agar bridge|Ag/AgCl. The preparation of PVC ion-selective electrode is described elsewhere (Shirahama et al., *Bull. Chem. Soc. Jpn.* 1981, 54: 375; Shirahama and Tashiro, *Bull. Chem. Soc. Jpn.* 1984, 57: 377; Mel'nikov et al., *J. Am. Chem. Soc.* 1995, 117: 9951). The electromotive force (emf) of the cell was measured with a digital Radiometer pHM-83 pH-meter. The electrode exhibited a good Nernstian response over the range of surfactant concentrations examined. Binding isotherms were obtained by titration of $5'10^{-4}$ base-mole/L polyethylene oxide-block-poly(sodium methacrylate) solutions with the solution of the corresponding surfactant. The results were corrected for the decrease in the copolymer concentration as a result of the addition of the surfactant solution. The fraction of occupied binding sites β was defined as follows $$\beta=(C_t-C_f)/C_i \quad (3)$$

where $C_t$ is the total concentration of added surfactant, $C_f$ is the concentration of the free surfactant, $C_f$ determined using the calibration curves (i.e., linear plots "emf vs. log $C_t$" determined in the absence of polymer and $C_t$<CMC), and $C_i$ is the concentration of ionic groups of the block copolymer. The results obtained for binding of cetylpyridinium bromide and dodecylpyridinium bromide are presented in FIG. 1.

EXAMPLE 5

The binding isotherms of doxorubicin (Sigma Co.) to polyethylene oxide-block-poly(sodium methacrylate) copolymer were determined using fluorescent spectroscopy. Briefly, the fluorescence emission intensity of doxorubicin at 556 nm (excitation 471 nm.) was determined in 10 mM phosphate buffer, pH 7.4 with and without the block copolymer. In the presence of block copolymer the fluorescence of doxorubicin was quenched. The fraction of occupied binding sites β was defined as follows $$\beta=\frac{I_o-I}{I_o}\cdot\frac{C_t}{C_i} \quad (4)$$

where $I_o$ and I are fluorescence emission intensities without and with the block copolymer, $C_t$ is the total concentration of added surfactant, and $C_i$ is the concentration of ionic groups of the block copolymer. The results obtained for binding of doxorubicin to polyethylene oxide-block-poly (sodium methacrylate) are presented in FIG. 2 (curve 1).

EXAMPLE 6

Following the procedure of Example 2 but replacing doxorubicin with rhodamine 123 (Sigma Co.), conducting fluorescence measurements at excitation 505 nm and emission 522 nm, and using $$\beta=\frac{I-I_o}{I_{max}-I_o}\cdot\frac{C_t}{C_i} \quad (5)$$

where $I_{max}$ is the maximal fluorescence at saturating concentrations of the block copolymer there is obtained the binding isotherm in FIG. 2 (curve 2).

EXAMPLE 7

Polyethylene oxide-block-poly(sodium methacrylate) was the same as described in Example 4. The homopolymer polymethacrylic acid with a Pw=930 was obtained by radical polymerization (Lipatov, and Zubov, Vysokomol. Soedin., Ser. A. 1959, 1:88). Complexes formed between these polymers and cetylpyridinium bromide (Sigma Co.)

were studied using turbidity measurements. At base molar concentrations of anionic polymers $1.08 \cdot 10^{-3}$ base-mole/L; temperature 25° C., and pH 9.2. The turbidity measurements were carried out using a Shimadzu UV160 spectrophotometer at 420 nm after equilibration of the system typically for 3 minutes. The data are reported in FIG. 3 as (100-T)/100, where T is transmission (%) for complexes from polyethylene oxide-block-poly(sodium methacrylate) and poly(sodium methacrylate).

EXAMPLE 8

The complexes between N-cetylpyridinium bromide and polyethylene oxide-block-poly(sodium methacrylate) were prepared in $8 \cdot 10^{-4}$ base-mole/L solution of the block copolymer at 25° C. and pH 9.2. The $C_t/C_i$ was varied from 0.01 to 5, where $C_t$ is the total concentration of added surfactant, and $C_i$ is the concentration of ionic groups of the block copolymer. Electrophoretic mobility (EPM) measurements were performed at 25° C. with an electric field strength of 15–18 V/cm by using "ZetaPlus" Zeta Potential Analyzer (Brookhaven Instrument Co.) with 15 mV solid state laser operated at a laser wavelength of 635 nm. The zeta-potential of the particles was calculated from the EPM values using the Smoluchowski equation. Effective hydrodynamic diameter was measured by photon correlation spectroscopy using the same instrument equipped with the Multi Angle Option. All solutions were prepared using double distilled water and were filtered repeatedly through the Millipore membrane with pore size 0.22 µM. The sizing measurements were performed at 25° C. at an angle of 90°. The results are presented in FIG. 4.

EXAMPLE 9

The interaction between a cationic surfactant (S+) and a weak polyacid represents an ion exchange reaction resulting in the release of the protons in accordance with the following scheme:

$$(\!-\!COOH)_n + nS^+ \rightleftharpoons [\!-\!COO^{-S+}]_n + nH^+ \qquad (6)$$

The equilibrium of this reaction for the mixtures of cetylpyridinium bromide with polyethylene oxide-block-poly methacrylic acid was studied at different pH by potentiometric titration (see, for example, Kabanov, Polymer Science 1994, 36:143). Polyethylene oxide-block-poly methacrylic acid was synthesized as described in Example 4. The alkali titration curves were obtained for the mixtures of N-cetylpyridinium bromide (Sigma Co.) with polyethylene oxide-block-poly methacrylic acid. The total concentration of the surfactant was equal to the concentration of the ionizable groups of the polyacid. The degree of conversion, θ, in the ion exchange reaction (5) was determined from original titration curves on the assumption that all alkali is consumed for neutralization of protons released as a result of this reaction. For a weak polyacid θ at a given pH is expressed as follows

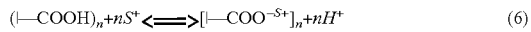

$$\theta = \left(m_b/V + [H^+] - \sqrt{K_a C_o}\right)/C_o, \qquad (7)$$

where $M_b$ is the number of moles of the added base, V is the current volume of the reaction system, $K_a$ is the characteristic dissociation constant, $C_o$ is the base-molar concentration of the polyacid. The results are presented in FIG. 5.

EXAMPLE 10

The existence of internal aqueous volume in the particles of the complex formed between the block copolymers and surfactants of the present invention can be conveniently demonstrated using a water-soluble fluorescent dye, 5,6-carboxyfluorescein. See, for example, Parker, Photoluminiscence of Solutions; Elsevier: New York, p. 303 et seq., 1968. The complex between N-cetylpyridinium bromide and polyethylene oxide-block-poly(sodium methacrylate) is prepared as described in Example 8 at Ct/Ci=1 replacing the solution of the copolymer in water for the solution of the same copolymer in 10 mM of 5,6-carboxyfluorescein (Sigma Co.). Briefly, 0.87 ml of the aqueous solution of 10 mM 5,6-carboxyfluorescein, pH 7.4 is mixed with 50 µl of 0.039 M solution of polyethylene oxide-block-poly(sodium methacrylate) and 80 µl of 0.025 M N-cetylpyridinium bromide solution. After 30 minutes incubation at room temperature the particles of the complex were separated from the dye remaining in the external volume by gel permeation chromatography using Sephadex G-25 medium (Pharmacia Biotech) equilibrated with the solution of 0.01 mM N-cetylpyridinium bromide. The fluorescence emission of 5,6-carboxyfluorescein in the solutions obtained is determined at the excitation wavelength 495 nm and 25° C. using Shimadzu 5000 spectrofluorimeter. The maximum of fluorescence emission of the dye in this system was observed at 517.2 nm (slit 1.5 nm) which corresponds to the emission maximum of the free dye in the absence of the particles. Addition of 40 µl of 10% (v/v) aqueous Triton X-100 (Sigma Co.) to this system results in a sharp increase in the fluorescence intensity resulting from the release of the concentrated dye from the internal aqueous cavity of the particles. This suggests that the particles represent the vesicles with an internal aqueous volume.

EXAMPLE 11

The complex between N-cetylpyridinium bromide and polyethylene oxide-block-poly(sodium methacrylate) was prepared as described in Example 10 replacing 10 mM 5,6-carboxyfluorescein solution with 0.1 mM solution of calcein (Sigma Co.). The particles of this complex were separated by gel permeation chromatography as described in Example 10. The fluorescence emission intensity of calcein was determined at the emission and excitation wavelengths 490 nm and 520 nm respectively. 2 µl of $CoCl_2$ solution and 40 µl of 10% Triton X-100 were added to this system in different order to quench fluorescence outside the vesicles. Addition of CoCl2 resulted in the decrease of the fluorescence in this system to 3% of the initial fluorescence. When Triton X-100 was added after $CoCl_2$ the fluorescence was further decreased to 1% of the initial value. In contrast, when Triton X-100 was added without prior addition of CoCl2 no change in the fluorescence was recorded. When CoCl2 solution was added after the Triton X-100 solution the fluorescence was decreased to about 1% of the initial value. This suggests formation of the vesicles with an internal volume of about 2% of the total volume.

EXAMPLE 12

A polyethyleneglycol (8,000)-polyethylene imine (m.w. 2,000) copolymer was synthesized as previously reported by Vinogradov et al. (Pharm. Res., 14: S-641). The complex between the polyethylene glycol-polyethyleneimine copolymer and anionic surfactant, Aerosol (OT (Sigma Co.) was obtained at $C_t/C_i=1$, where $C_t$ is the total concentration of added surfactant, and $C_i$ is the concentration of ionic groups of the block copolymer. The size of the particles formed, determined by dynamic light scattering as described in Example 8, equals 57 nm.

EXAMPLE 13

The complex between the polyethylene glycol-polyethyleneimine copolymer, exemplified above, and fatty acid salt, oleic acid sodium salt (Sigma Co.) was obtained at $C_t-C_i=1$ in sodium phosphate buffer (SPB), 10 mM, pH 6.0 by simple mixing of the copolymer solution in the same buffer and fatty acid salt solution in methanol. The final content of methanol in the complex solution was 3%. The size of the particles formed, determined by dynamic light scattering as described in Example 8, above, was 54 nm.

EXAMPLE 14

The complex between the polyethylene glycol-polyethyleneimine copolymer, mentioned above, and fatty acid salt, oleic acid sodium salt was obtained at $C_t-C_i=1$ in sodium phosphate buffer (SPB), 10 mM, pH 7.4, as described in Example 13, above. The size of the particles formed, determined by dynamic light scattering as described in Example 8, above, was 44 nm.

EXAMPLE 15

The complex between the polyethylene glycol-polyethyleneimine copolymer, mentioned above, and fatty acid salt, oleic acid sodium salt was obtained at $C_t-C_i=1$ in TRIS-buffer, 10 nM, pH 8.2, as described in Example 13, above. The size of the particles formed, determined by dynamic light scattering as described in Example 8, above, was 56 nm.

EXAMPLE 16

The complex between the polyethylene glycol-polyethyleneimine copolymer and retinoic acid (Aldrich Co.) was obtained at $C_t-C_i=1$ in sodium phosphate buffer (SPB), 10 mM, pH 7.4. The solution of retinoic acid in water/methanol (60:40, v/v) mixture containing sodium hydroxide was added to the copolymer solution in the SPB. The final content of methanol in the complex solution was 5%. The additional absorption band ($\lambda_{max}$ =306 nm) in the UV-vis spectrum of retinoic acid in the presence of copolymer was found to be comparable to that of pure retinoic acid at the same conditions ($\lambda_{max}$=343 nm).

EXAMPLE 17

42.8 mg of nonafluoropentanoic acid (Aldrich Co.) and 1 mg of Taxol were mixed in 50 μl of ethanol containing sodium hydroxide ($2.84 \times 10^{-4}$ mole). This mixture was added to 1 ml of the complex between the polyethylene glycol-polyethyleneimine copolymer and oleic acid sodium salt prepared as described in Example 13, above. After stirring overnight, the sample was centrifuged 10 minutes at 13000 RPM. 20 μl of supernatant was added to 1 ml of methanol and UV spectra were recorded. The Taxol concentration was calculated from the absorbency at 227 nm ($\epsilon$=44,359 ml/mg). The extinction coefficient was estimated in the presence of fluoroorganic component in methanol. The degree of Taxol solubilization was 74.4%. The size of the complex particles loaded with the Taxol/Fluoroorganic compound mixture determined by dynamic light scattering as described in Example 8, above, was 61 nm.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

What is claimed is:

1. A composition of matter comprising a supramolecular complex which comprises as constituents a block copolymer, having at least one nonionic, water soluble segment and at least one polyanionic segment, and at least one charged surfactant having hydrophobic groups, the charge of said surfactant being opposite to the charge of the polyanionic segment of said block copolymer, wherein the block copolymer constituent is not cross-linked to form networks the constituents of said complex are bound by interaction between said opposite charges and between surfactant hydrophobic groups, and the ratio of the net charge of said surfactant to the net charge of the polyanionic segment present in said block copolymer constituent of said complex is between about 0.01 and about 100.

2. A composition as claimed in claim 1, wherein the nonionic segment of said block copolymer is selected from the group consisting of polyetherglycols, copolymers of ethylene oxide and propylene oxide, polysaccharides, homopolymers and copolymers of vinyl compounds selected from the group consisting of acrylamide, acrylic acid esters, methacrylamide, methacrylic acid esters, N-(2-hydroxypropyl) methacrylamide, vinyl alcohol, vinyl pyrrolidone, vinyl triazole, or the N-oxide of vinylpyridine and polyorthoesters.

3. A composition as claimed in claim 1 in the form of vesicles.

4. A composition as claimed in claim 1, wherein said polyanionic segment is selected from the group consisting of polymethacrylic acid and its salts, polyacrylic acid and its salts, copolymers of methacrylic acid and its salts, copolymers of acrylic acid and its salts, heparin, poly(phosphate), polymaleic acid, polylactic acid, nucleic acid or carboxylated dextran.

5. A composition as claimed in claim 1, wherein said polyanionic segment is a homopolymer or a co-polymer prepared from a monomer which polymerizes to form a product with carboxyl pendant groups, said monomer being selected, from the group consisting of acrylic acid, aspartic acid (amino acid), 1,4-phenylenediacrylic acid citraconic acid, citraconic anhydride, trans cinnamic acid, 4-hydroxy-3-methoxy cinnamic acid, p-hydroxy cinnamic acid, trans-glutaconic acid, glutamic acid (amino acid), itaconic acid, linoleic acid, linolenic acid, methacrylic acid, maleic acid, maleic anhydride, mesaconic acid, trans-p-hydromuconic acid, trans-traumatic acid, benzoic acid, vinyl glycolic acid.

6. A composition as claimed in claim 1, wherein said surfactant is selected from the group consisting of lipophilic quaternary ammonium salts, lipopolyamines, lipophilic polyamino acids, lipophilic primary-, secondary-, tertiary- and heterocyclic amines, lipophilic imidazoles, lipophilic piperidinium salts, lipophilic quinaldinium salts, lipophilic azonium and azolium salts, pH-sensitive cationic lipids, dicationic bolaform electrolytes or a mixture of said surfactants.

7. A composition as claimed in claim 1, further including a nonionic surfactant.

8. A composition as claimed in claim 7, wherein said nonionic surfactant is selected from the group consisting of dioleoyl phosphatidylethanolamine, dioleoyl phosphatidylcholine, or a mixture of said nonionic surfactants.

9. A composition of matter forming a supramolecular complex in aqueous medium and comprising as constituents a block copolymer, having at least one nonionic, water soluble segment and at least one polycationic segment, and at, least one charged surfactant having hydrophobic groups, the charge of said surfactant being opposite to the charge of the polycationic segment of said block copolymer, the constituents of said complex being bound by interaction between said opposite charges and between surfactant hydrophobic groups, with the proviso that when said charged surfactant has a biological activity, said charged surfactant has a net charge of no more than about 10, the ratio of the net charge of said surfactant to the net charge of the polycationic segment present in said block copolymer constituent of said complex is between about 0.01 and about 100, and said supramolecular complex has a particle size of less than 500 nm.

10. A composition as claimed in claim 9 in the form of vesicles.

11. A composition as claimed in claim 9, wherein said polycationic segment is selected from the group consisting of polyamino acid, alkanolamine esters of polymethacrylic acid, polyamides, polyalkyleneimines, polyvinyl pyridine and the quaternary ammonium salts of said polycationic segment.

12. A composition as claimed in claim 9, comprising an anionic surfactant selected from the group consisting of alkyl sulfates, alkyl sulfonates, fatty acid soaps, salts of hydrox-, hydroperoxy-, polyhydroxy-, epoxy-fatty acids, salts of mono- and polycarboxylic acids, prostanoic acid and prostaglandins, leukotrienes and lipoxines, alkyl phosphates, alkyl phosphonates, sodium-dialkyl sufosuccinate, n-alkyl ethoxylated sulfates, cholate and desoxycholate of bile salts, perfluorocarboxylic acids, fluoroacliphatic phosphonates, fluoroaliphatic sulphates.

13. A composition as claimed in claim 1, wherein said surfactant is a biologically active agent.

14. A composition as claimed in claim 13, wherein said biological active agent has a molecular mass of less than about 2000.

15. A method for preparing a composition of matter in the form of vesicles, said method comprising mixing a block copolymer, having at least one nonionic, water soluble segment and at least one polyionic segment, and a charged surfactant having hydrophobic groups, the charge of said surfactant being opposite to the charge of the polyionic segment of said block copolymer, the ratio of the net charge of said surfactant to the net charge of said surfactant to the net charge of the polyionic segment present in said block copolymer being between about 0.01 and about 100, and with the proviso that when said surfactant is a biologically active agent, said agent has a net charge of no more than about 5.

16. A method as claimed in claim 15, wherein said the polyionic segment of said block copolymer is polyanionic.

17. A method as claimed in claim 15, wherein said the polyionic segment of said block copolymer is polycationic.

18. A composition as claimed in claim 1, wherein said charged ratio is between about 0.1 and about 10.

19. A composition as claimed in claim 9, wherein said charged ratio is between about 0.1 and about 10.

20. A composition as claimed in claim 9, wherein said supramolecular complex has a particle size less than 200 nm.

21. A composition as claimed in claim 9, wherein said supramolecular complex has a particle size less than 100 nm.

22. A composition as claimed in claim 9, wherein said surfactant is a biologically active agent.

23. A composition as claimed in claim 22, wherein said biological active agent has a molecular mass of less than about 2000.

24. The composition of claim 5, where said copolymer also comprises at least one monomer selected from the group consisting of 2-propene-1-sulfonic acid, 4-styrene sulfonic acid, vinylsulfonic acid and vinyl phosphate acid.

* * * * *